United States Patent
Hiroi et al.

(10) Patent No.: US 6,898,305 B2
(45) Date of Patent: May 24, 2005

(54) CIRCUIT PATTERN INSPECTION METHOD AND APPARATUS

(75) Inventors: Takashi Hiroi, Yokohama (JP); Masahiro Watanabe, Yokohama (JP); Chie Shishido, Yokohama (JP); Asahiro Kuni, Tokyo (JP); Maki Tanaka, Yokohama (JP); Hiroshi Miyai, Yokohama (JP); Yasuhiko Nara, Hitachinaka (JP); Mari Nozoe, Hino (JP)

(73) Assignee: Hitachi, Ltd., Tokyo (JP)

( * ) Notice: Subject to any disclaimer, the term of this patent is extended or adjusted under 35 U.S.C. 154(b) by 661 days.

(21) Appl. No.: 09/791,911

(22) Filed: Feb. 22, 2001

(65) Prior Publication Data

US 2002/0114506 A1 Aug. 22, 2002

(51) Int. Cl.[7] .................................................. G06K 9/00
(52) U.S. Cl. ........................ 382/149; 382/147; 382/172; 356/394
(58) Field of Search .............................. 382/149, 141, 382/278, 164, 168, 151, 205, 147, 172, 155; 250/310, 307, 208.1, 554; 324/210; 73/105, 117.3; 356/601, 399, 394

(56) References Cited

U.S. PATENT DOCUMENTS

| 4,628,531 A | * | 12/1986 | Okamoto et al. ............ 382/144 |
| 5,146,509 A | * | 9/1992 | Hara et al. ................... 382/149 |
| 5,153,444 A | * | 10/1992 | Maeda et al. ........... 250/559.05 |
| 5,502,306 A | | 3/1996 | Meisburger et al. |
| 5,640,200 A | * | 6/1997 | Michael ....................... 348/87 |
| 6,087,673 A | | 7/2000 | Shishido et al. |
| 6,363,167 B1 | * | 3/2002 | Miyano et al. ............. 382/145 |
| 6,678,404 B1 | * | 1/2004 | Lee et al. .................... 382/155 |

OTHER PUBLICATIONS

Abstract, JP App. 57-196377(A), "Pattern Recognizing Mehtod", Feb. 12, 1982.

* cited by examiner

*Primary Examiner*—Bhavesh M. Mehta
*Assistant Examiner*—Sheela Chawan
(74) *Attorney, Agent, or Firm*—Townsend and Townsend and Crew LLP

(57) ABSTRACT

The present invention provides techniques, including a method and system, for inspecting for defects in a circuit pattern on a semi-conductor material. One specific embodiment provides a trial inspection threshold setup method, where the initial threshold is modified after a defect analysis of trial inspection stored data. The modified threshold is then used as the threshold in actual inspection.

24 Claims, 21 Drawing Sheets

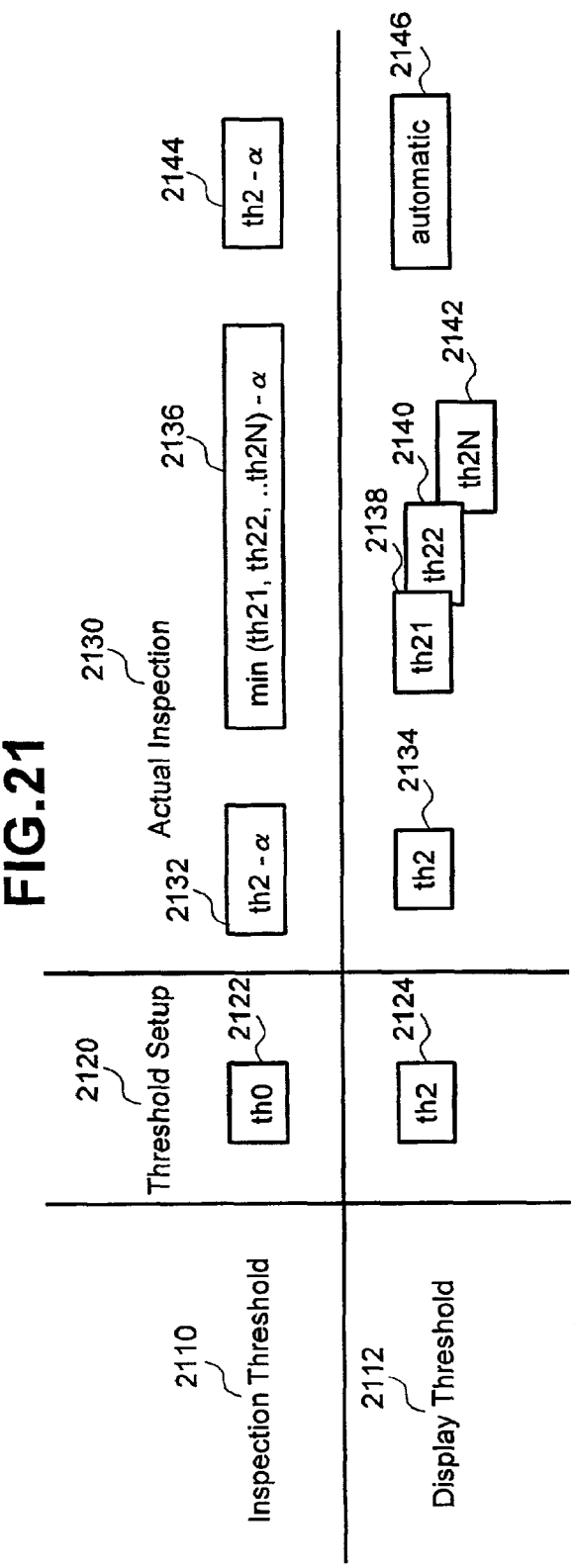
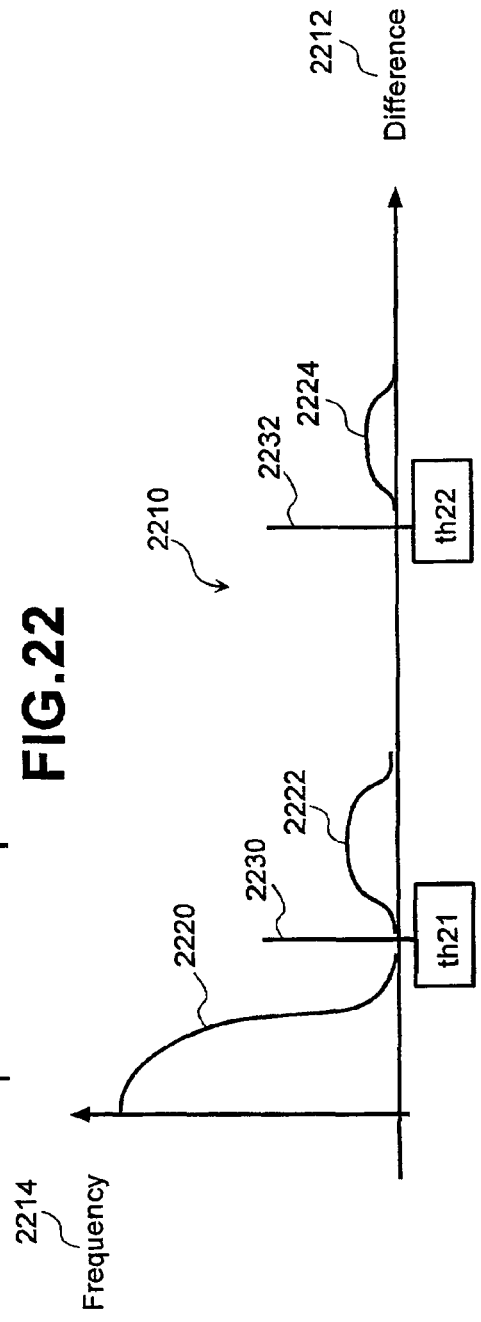
FIG.21
FIG.22

CIRCUIT PATTERN INSPECTION METHOD AND APPARATUS

CROSS-REFERENCES TO RELATED APPLICATIONS

The following commonly assigned, co-pending application is incorporated by reference in their entirety:

U.S. patent application Ser. No. 09/450,856, "Inspection Method, Apparatus and System for Circuit Pattern," by Nara Yasuhiko, et. al, filed Nov. 29, 1999.

BACKGROUND OF THE INVENTION

The present invention generally relates to inspection in a semiconductor manufacturing process and in particular to using an inspection system to inspect for defects in a circuit pattern on a semiconductor material. The circuit pattern may include, a Liquid Crystal Diode (LCD) display, a Thin Film Transistor (TFT) display, a memory matte, an integrated circuit, a photomask, a magnetic head, and the like. The inspection system may include a Semiconductor Electron Microscope (SEM) detection system, an optical detection system, a X-ray detection system, a Focus Beam Ion detection system, a Transparent Electron Microscope (TEM) detector system, a particle detection system, and the like.

FIG. 1 shows a simplified layout of a semiconductor wafer 100 which is a target of an inspection system. There are many die, for example, 110, 112, and 114 on the wafer 100. Normally each die has the same pattern on the wafer 100 for use in the same product.

FIGS. 2 and 3 each show a conventional inspection system (an example is given in U.S. Pat. No. 5,502,306, "Electron Beam Inspection System and Method," by Meisburger, et. al., issued Mar. 26, 1996. Another example is given in U.S. Pat. No. 6,087,673, "Method for Inspecting Pattern and Apparatus Thereof," by Shishido, et. al., issued Jul. 11, 2000) In the conventional system, a SEM Detecting Apparatus 208 is connected to an Image Processing System 228. The SEM Detecting Apparatus includes, an electron beam 210 from an electron source 212 sending electrons to a wafer 100 through an objective lens 214. The secondary electron emissions 216 from the wafer 100 are detected by a sensor 218. A beam deflector 220 causes the electron beam 210 to scan horizontally, while stage 222 movement causes a vertical scan. Thus a two dimensional (x-y) image is obtained. The resulting analog sensor signals are converted to digital data and this two-dimensional digital image is sent to Image Processing System 228 for defect detection.

In the Image Processing System 228 the first digital image is stored as a reference image. Another scan of a different potion of the wafer, produces a second digital image. This second image is the inspection image which may or may not be stored, and is compared with the reference image. As the two images are presumed to have the same pattern, a difference image is formed. The difference image is thresholded with an initial threshold, and when a defect image exists, a defect is determined to exist. Defect information such as defect position (x-y coordinates), size (area), x-projection size, and y-projection size is also generated. The defect information forms an entry in a defect list 232. The above process is repeated with the inspection image, i.e., second digital image, being stored as the reference image and overwriting the stored first digital image. A newly scanned image, i.e., third digital image, is the new inspection image and replaces the second digital image. The result of this repetitive process is a defect list 232. This defect list 232 is sent by the Image Processing System 228 to a Graphic User Interface (GUI) Console 230 for verification by the user. If the user desires to view a defect in the defect list 232, the positional information is used to re-scan the defect area and show the defect on the console 230.

The conventional Image Processing System 228 normally operates in one and only one of two detection modes at a time. One is a die to die comparison mode 234 (FIG. 2) and the other is an array comparison mode 236 (FIG. 3). The die to die comparison 234 compares one die image with the next die image, where each die belongs to the same product. Array comparison 236 compares a repeated pattern in, for example, a memory matte, on a die. Thus the conventional image processing system has a problem in that a mixture of die to die comparison and array comparison cannot be done in one scan of the wafer.

In the conventional system determining the threshold to be used in the difference images during actual inspection of the wafer 100 is very important. Since the defect image is determined from thresholding the difference image, too low a threshold may cause many false defects. Too high a threshold may miss many actual defects. Thus setting up the threshold is an important part of the inspection process.

FIG. 4 shows a conventional threshold setup method. At step 310 the user sets a value for the initial threshold based on the user's best guess as to the maximum noise level in the images. The initial threshold is typically set low and is raised to a higher value when applying this setup method. The user also selects a small region of the wafer for trial inspection. The conventional system, using the initial threshold, determines a defect list 232, including defect information (step 320), which is sent to the Graphical User Interface (GUI) console 230 for user evaluation. At step 330, the defect information is used to re-scan the defect locations on the wafer 100 and display the defects for verification. The user then verifies whether the defects are true or false defects. At step 340, if there are too few true defects or too many false defects, the user sets a new higher threshold, and the system goes back to step 310. Typically this loop must be repeated one to three times, before a final threshold is determined. In FIG. 4 user operation is indicated by a bold box 360. Thus step 310 and 330 involve user operation 360. This threshold setup method has several problems. First it is slow and manually intensive. Since defect images are not stored, rescanning is necessary to view the defect list 232 for verification. As scanning requires wafer stage 222 movement, this process takes time. If the user determines that the threshold is too low, the user must guess at a new level. The results of the threshold modification are available only after the small region is re-scanned during a second trial inspection. The above process is repeated several times and is slow. Another problem is that the repetitive re-scanning of the wafer 100 could alter the wafer surface and hence the inspection results. Lastly, no image data is retained for use in actual inspection or follow-up analysis, thus it is difficult to improve the process.

Therefore there is a need for a defect inspection method and system that is faster and more efficient. There is also a need for maintaining defect image data for use in, for example, trial inspection, defect analysis, actual inspection, and/or after inspection analysis.

SUMMARY OF THE INVENTION

The present invention provides techniques, including a method and system, for inspecting for defects in a circuit pattern on a semi-conductor material. One specific embodiment provides a trial inspection threshold setup method, where the initial threshold is modified after a defect analysis of trial inspection stored data. The modified threshold is then used as the threshold in actual inspection.

One embodiment of the present invention provides a method for inspecting a specimen, for example, a circuit pattern on a semiconductor wafer. The method includes: setting a threshold value. Next, a detected image of a specimen is detected and compared to a reference image; A defect candidate is then extracted using the threshold value and an information of the defect candidate is stored to a memory. A new threshold value is set and a defect is extracted from the defect candidate using the stored information and the new threshold value. The information of the defect may include at least one of the following: a defect candidate position, a defect candidate area, a defect candidate x and y projection size, a maximum difference between the detected image and the reference image, a defect texture, or a reference texture or an image of the defect candidate.

In an alternative embodiment of the present invention a method for inspecting a circuit pattern on a semiconductor material is provided. First an initial threshold is set. Next, an inspection image is detected. A defect candidate information, for example, a margin, is determined by thresholding a comparison between the inspection image and a reference image, where the thresholding uses the initial threshold. A new threshold is determined using the defect candidate information and a defect in the inspection image is evaluated using said new threshold.

Another embodiment of the present invention stores raw images received from a detector system, for example, a Semiconductor Electron Microscope (SEM) detecting apparatus, which scans dies on a semi-conductor wafer. An initial threshold is set from an average of the electron beam noise. From the stored raw images, inspection images and corresponding reference images are extracted using die to die comparison and/or array comparison. A difference between an inspection image and its corresponding reference image is thresholded, using the initial threshold, to determine if a potential or candidate defect exists in the inspection image. The defect is, at this stage a potential or candidate defect, as it later will be verified by the user to be either a true or a false defect. Clipped images of the inspection and reference images, along with defect candidate information, are stored in a computer readable medium. Next using the clipped images of the inspection and reference images, a defect distribution is obtained. Using this defect distribution a new threshold is determined. A GUI display is provided showing a two dimensional defect distribution with symbols representing the defect candidates with thresholds equal to or above the new threshold. By selecting a symbol the user can verify the defect, as a true or false defect, in an expanded view, showing, for example, the clipped inspection image associated with the symbol. After verifying a plurality of defect candidates, the user may set another threshold, and again view the results responsive to this other threshold. As the images are stored re-scanning is not necessary. The end result is a threshold that may be used for actual inspection. This threshold is obtained faster and more efficiently than the conventional method. In addition, the stored images may be used for actual inspection and after inspection analysis.

One embodiment of the present invention provides a method, using a computer, for performing defect analysis on a plurality of images from an inspection system. The method includes, storing the plurality of images in a computer readable medium; retrieving an inspection image from a first image of the stored plurality of images; retrieving a corresponding reference image from a second image of the stored plurality of images; and analyzing the inspection image and corresponding reference image to determine if a true defect exists. In addition, in some cases the first and second image may be the same image.

A second embodiment of the present invention provides a method, using a computer, for inspecting for defects in a circuit pattern, including determining if there is a defect candidate image, by thresholding a difference image, where the difference image comprises the difference between an inspection image and a corresponding reference image. And if there is a defect candidate image, storing a clipped inspection image and a corresponding clipped reference image. In addition defect candidate information, including, defect candidate positional coordinates, is stored. A margin is also determined using the clipped inspection image and the clipped reference image. Optionally, calculations for determining a classification, a threshold for a type of defect, or an enhanced result may be done.

A third embodiment of the present invention provides an inspection system for examining a plurality of images having potential defects in a circuit pattern on a semiconductor material. The system includes, a defect image memory for storing clipped images of the plurality of images; an image analyzer, comprising a plurality of processors, coupled with the defect image memory, for analyzing the clipped images retrieved from the defect image memory; and a non-volatile storage coupled with the image analyzer for storing the clipped images and results of the analyzing.

A forth embodiment of the present invention provides a method for detecting defects in a circuit pattern on a semiconductor material using an inspection system. First, a plurality of scanned images from a detecting apparatus are stored. Next an inspection image and a reference image are determined from the plurality of scanned images based on a selection of either die to die comparison or array comparison. And using the inspection image and the reference image, a defect candidate image is determined.

A fifth embodiment of the present invention provides an image processing system for detecting defects in a circuit pattern on a semiconductor material using images from a detecting apparatus. The image processing system includes, an image memory for storing the images; and a defect detection image processing module for detecting defect candidate information from stored images, where the stored images include an inspection image and/or a reference image.

A sixth embodiment of the present invention provides a method for determining an updated threshold for use in actual inspection of a semiconductor wafer. The method includes: setting an initial threshold; determining a plurality of difference metrics using the initial threshold; determining a difference distribution based on the plurality of difference metrics; and determining the updated threshold based on an evaluation of the difference distribution.

A seventh embodiment of the present invention provides a method of resetting a threshold using a display coupled with a computer. The method includes, displaying a first threshold value, were the first threshold value is used to select the defect candidate image indications to be shown on a defect candidate distribution screen of the display; changing the first threshold value to a second threshold value, wherein the defect candidate image indications on the defect distribution screen change responsive to the second threshold.

A eighth embodiment of the present invention provides a method in a computer system for determining a threshold for use in actual inspection of a semiconductor material, comprising a circuit pattern. A first threshold and a second threshold are displayed. In addition a graphic representation of a defect candidate image with a margin greater than or equal to the second threshold minus the first threshold is displayed; Next, when the graphic representation of the defect candidate image is selected for expanded viewing, a clipped image associated with the graphic representation is shown; and when the defect candidate image is a false defect, and a predetermined number of allowable false defects is exceeded, a new second threshold is received from the user. The selected clipped image is selected from a group consisting of a clipped inspection image, a clipped reference image, or a clipped defect candidate image.

A ninth embodiment of the present invention provides a method in a computer system for displaying a defect candidate, where the defect candidate is stored in a memory. The method includes: displaying a two-dimensional defect candidate distribution for a threshold on a first screen, the two-dimensional defect candidate distribution including an indication of the defect candidate; and displaying on a second screen an expanded view of the defect candidate, responsive to a selection of the indication on the first screen.

A tenth embodiment of the present invention provides a distributed system for inspecting semiconductor circuit pattern defects. The system includes: an inspection apparatus for acquiring a plurality of images associated with the semiconductor circuit pattern defects and for performing defect analysis on a plurality of stored images; a server connected to the inspection apparatus via a communications network for storing the plurality of images, and for providing access to the plurality of stored images; and a client computer connected to the server and the inspection apparatus via the communications network for displaying a plurality of symbols associated with selected images of the plurality of stored images in response to selection of the selected images by the defect analysis. In an alternative embodiment the defect analysis is performed by the server instead of the inspection apparatus.

A eleventh embodiment of the present invention provides a method for determining an inspection threshold used in actual defect inspection of a semiconductor. First, a first threshold using a defect difference distribution is calculated; next a second threshold based on said first threshold is stored in a computer readable medium and then used in actual inspection.

In another embodiment of the present invention a method for determining a selected threshold of a plurality of thresholds, where the plurality is used in actual defect inspection of a semiconductor, is provided. The method includes: determining the plurality of thresholds from a defect difference distribution; displaying to a user an indication, such as a user selectable button, for each of the plurality of thresholds; and responsive to a user selection of a selected threshold, displaying symbols of defects with differences greater than or equal to the selected threshold.

These and other embodiments of the present invention are described in more detail in conjunction with the text below and attached figures.

BRIEF DESCRIPTION OF THE DRAWINGS

FIG. 21 shows thresholds that may be used in actual inspection 2130 of an embodiment of the present invention; and FIG. 22 shows an example of defect difference distributions of an embodiment of the present invention.

DESCRIPTION OF THE SPECIFIC EMBODIMENTS

Figure 1:
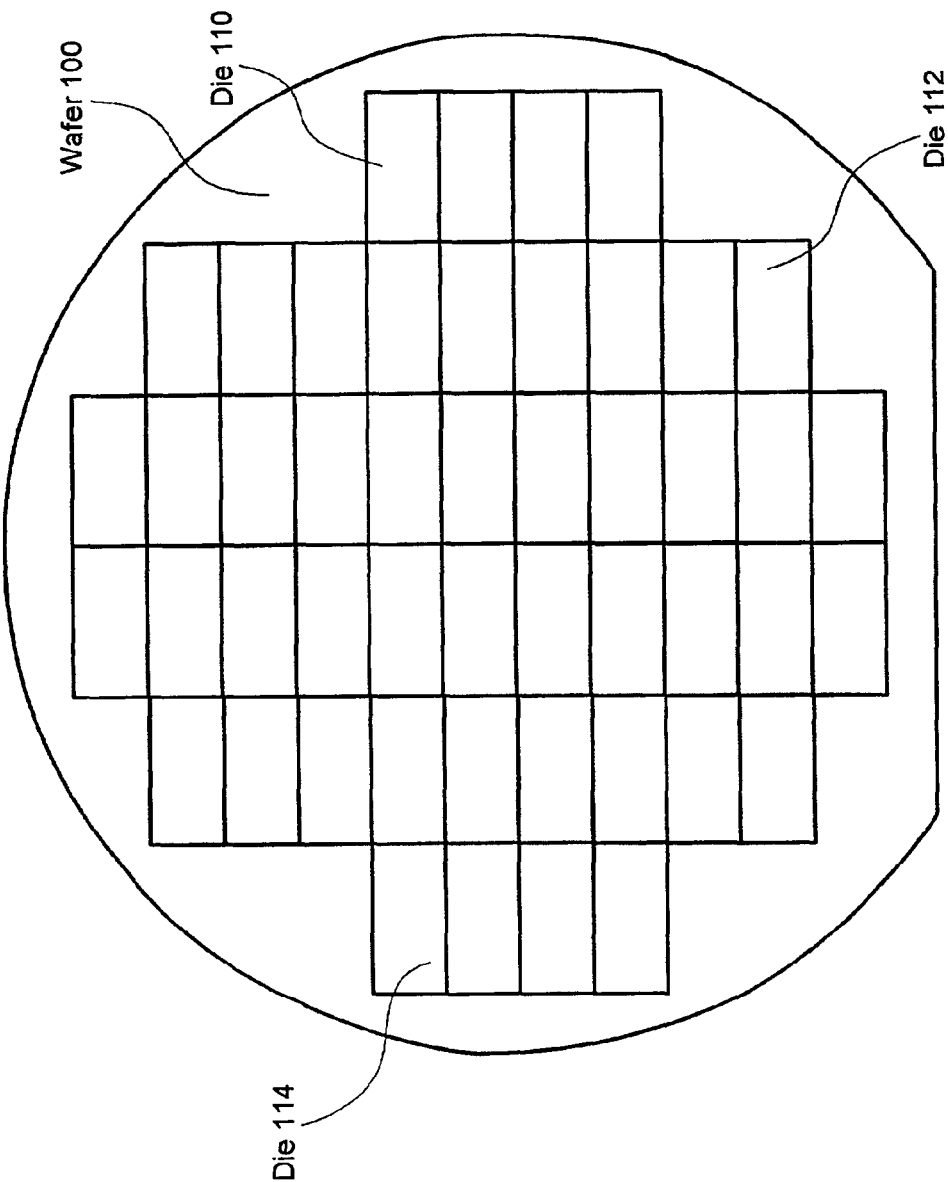
FIG. 1 shows a simplified layout of a semiconductor wafer which is a target of an inspection system.
Figure 2:
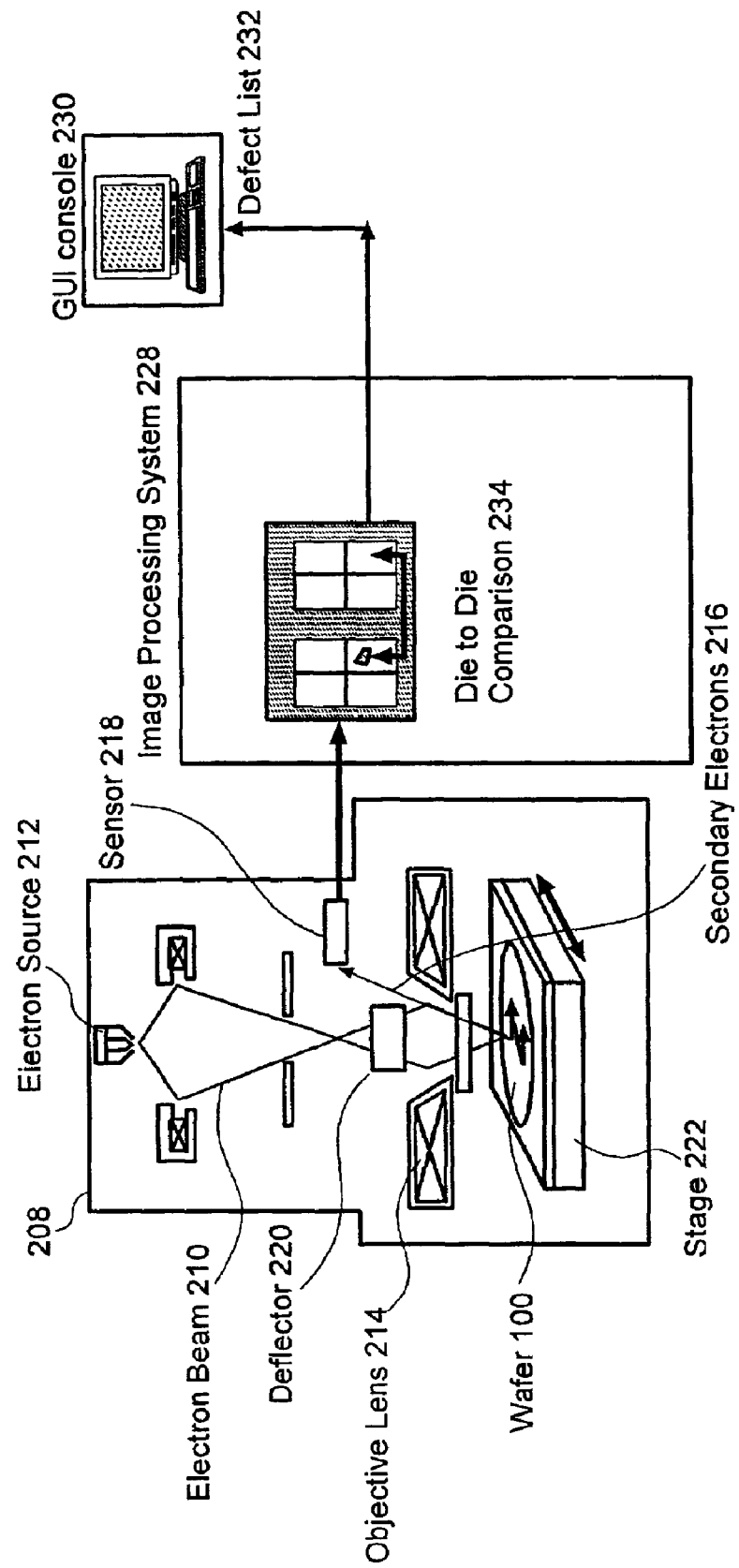
FIGS. 2 and 3 each show a conventional inspection system.
Figure 3:
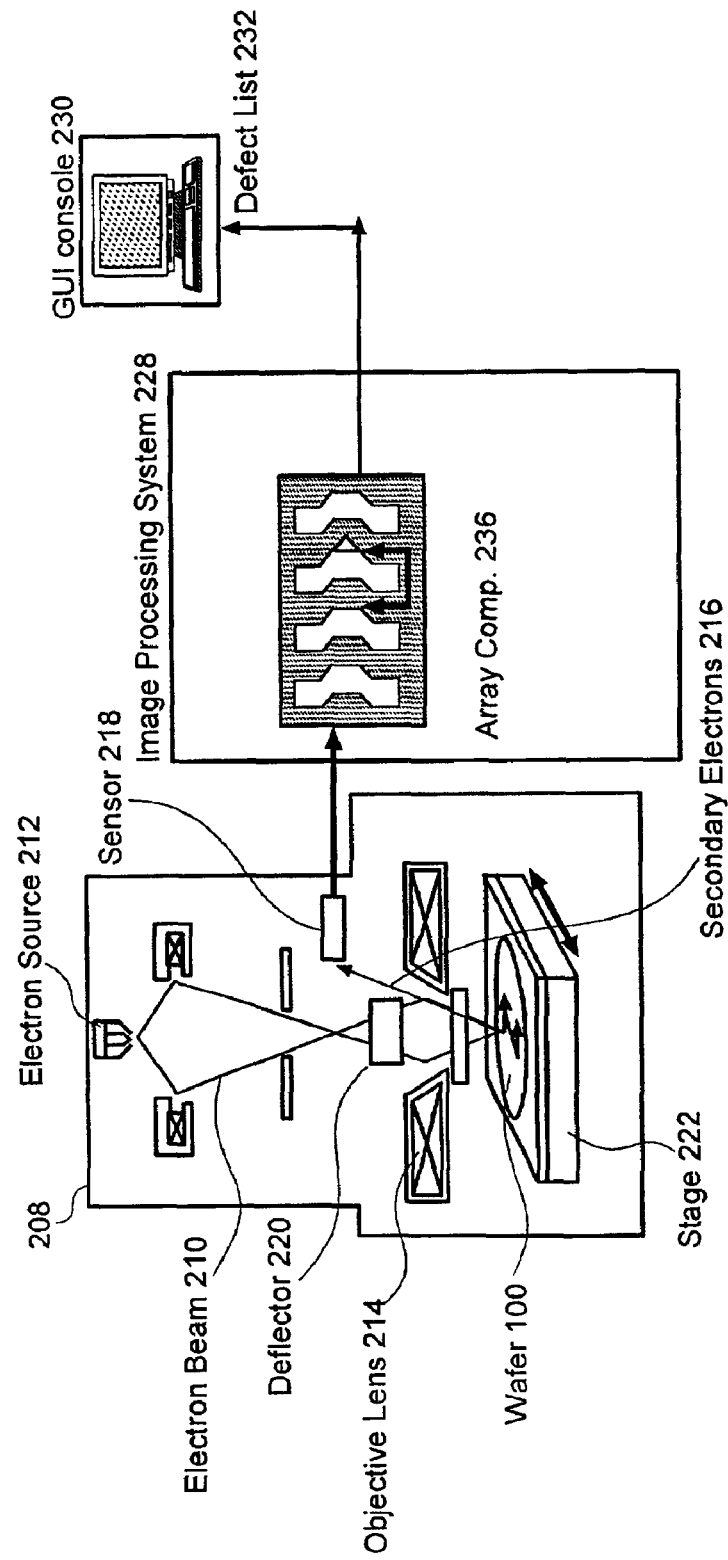
Figure 4:
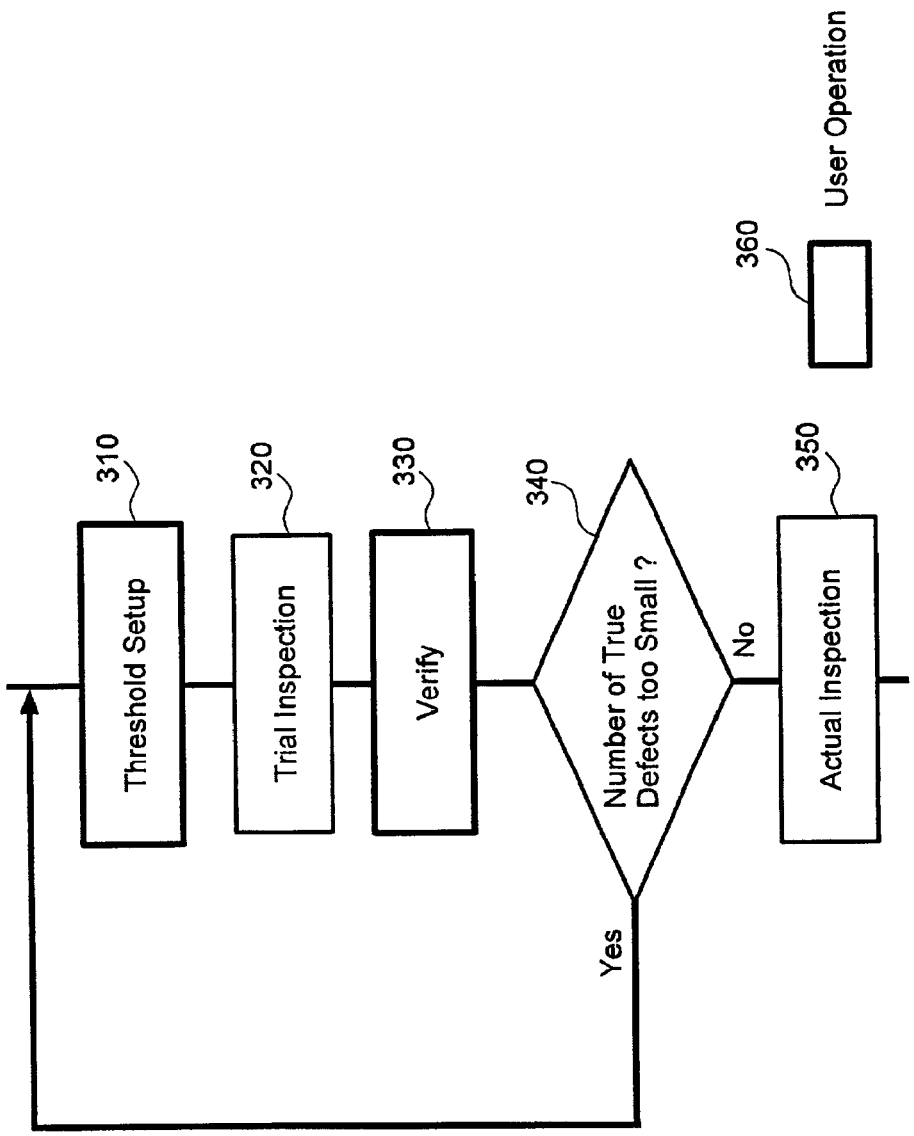
FIG. 4 shows a conventional threshold setup method.
Figure 5:
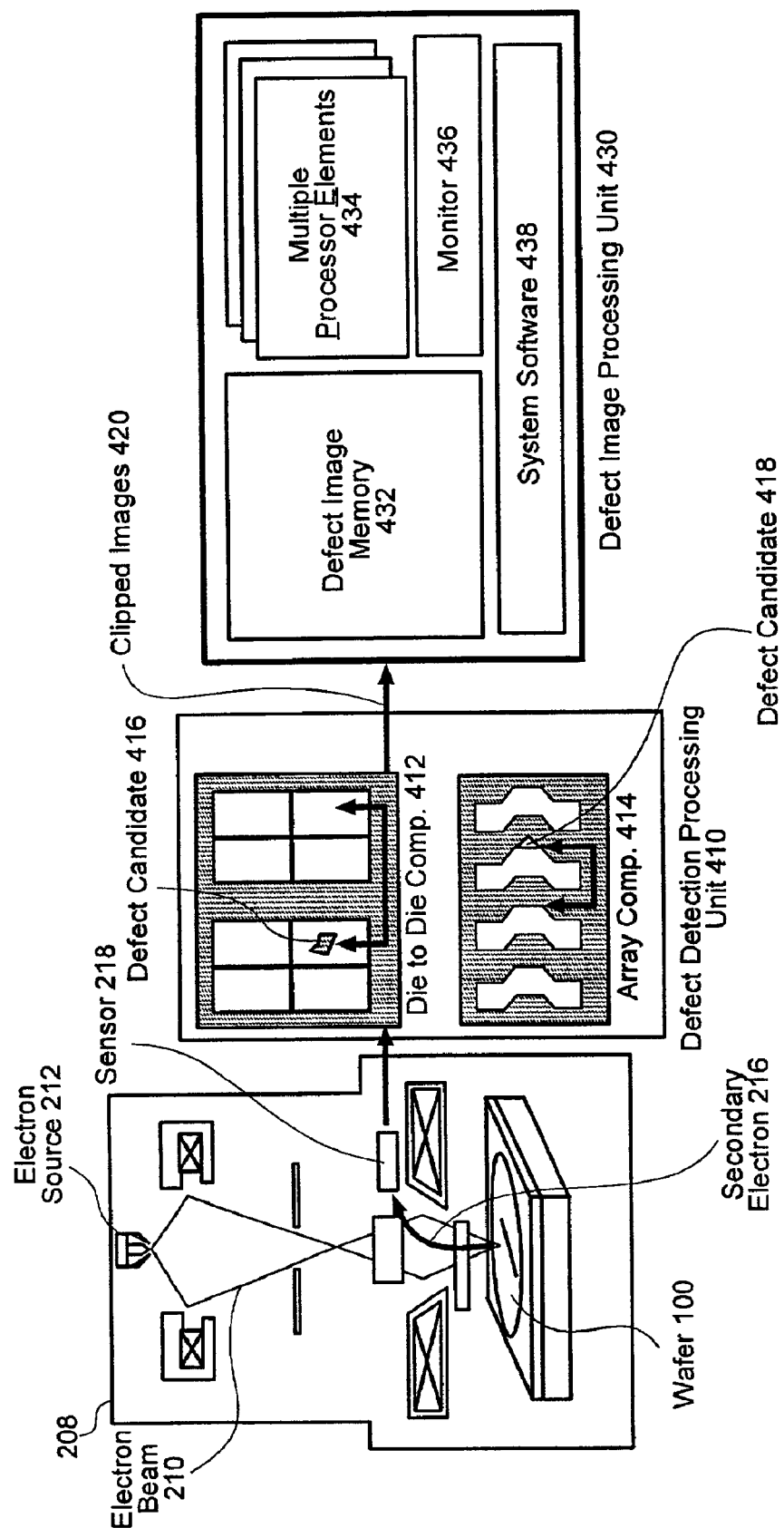
FIG. 5 shows a simplified block diagram of an embodiment of an inspection system of the present invention.

FIG. 5 shows a simplified block diagram of an embodiment of an inspection system of the present invention. The embodiment of the inspection system includes a Defect Detection Processing Unit 410 and a Defect Image Processing Unit 430. A SEM detection apparatus 208 is coupled with a Defect Detection Processing Unit 410. The SEM Detection Apparatus 208 is the same as in FIGS. 2 and 3. The Defect Detection Processing Unit 410 includes an image memory (not shown) for storing the two dimensional (x-y) images from the SEM Detection Apparatus 208, a die to die comparison module 412 and an array comparison module 414. The images stored in image memory are raw images of the scan of the wafer 100 by the SEM Detection Apparatus 208. The image memory may include images of an entire wafer 100 or a section of the wafer. If only a section of the wafer is included, the image memory acts as a buffer or queue, inputting new raw images from the SEM Detection Apparatus 208 and outputting raw images to be processed by die to die comparison module 412 or the array comparison module 414. Since raw images are stored, either die to die comparison or array comparison may be done with one scan. A user via a control console inputs into the Defect Detection Processing Unit 410, the wafer and die layout. The input includes, a die pitch which is used in die to die comparison and a cell pitch which is used in array comparison. The die to die comparison module 412 has function similar to the die to die comparison 234 performed in the Image Processing System 228 of FIG. 2, but in the Defect Detection Processing Unit 410, a defect candidate 416 is produced rather than an entry in a defect list 232. In addition the Defect Detection Processing Unit 410 has an array comparison module 414 for performing an array comparison like 236 in Image Processing System 228 of FIG. 3, and it also produces a defect candidate 418. A defect candidate is a potential defect, which may be a true, i.e., actual, or a false defect. On one or more of the defect candidates, the user will later verify, whether the defect candidate represents a true or false defect. When a defect candidate, for example 416 or 418, is determined to exists, clipped images, including a clipped inspection image having the defect candidate, and a corresponding clipped reference image (and optionally a clipped defect candidate image), and defect candidate information is outputted by the Defect Detection Processing Unit 410 to the Defect Image Processing Unit 430. The Defect Detection Processing Unit 410 has program code for clipping the images and for determining the defect candidate information, for example, defect candidate position, area, x & y projection sizes, and optionally a margin.

The Defect Image Processing Unit 430 includes, a Defect Image Memory 432, Multiple Processor Elements 434, a Monitor 436, and System Software 438. The Defect Image Memory 432 receives and stores the clipped images 420 and the defect candidate information from the Defect Detection Processing Unit 410. The Multiple Processor Elements 434, include one or more processors, and perform the defect analysis on the data stored in Defect Image Memory 432 using System Software 438. The defect analysis results are displayed to the user on Monitor 436.

Figure 6:
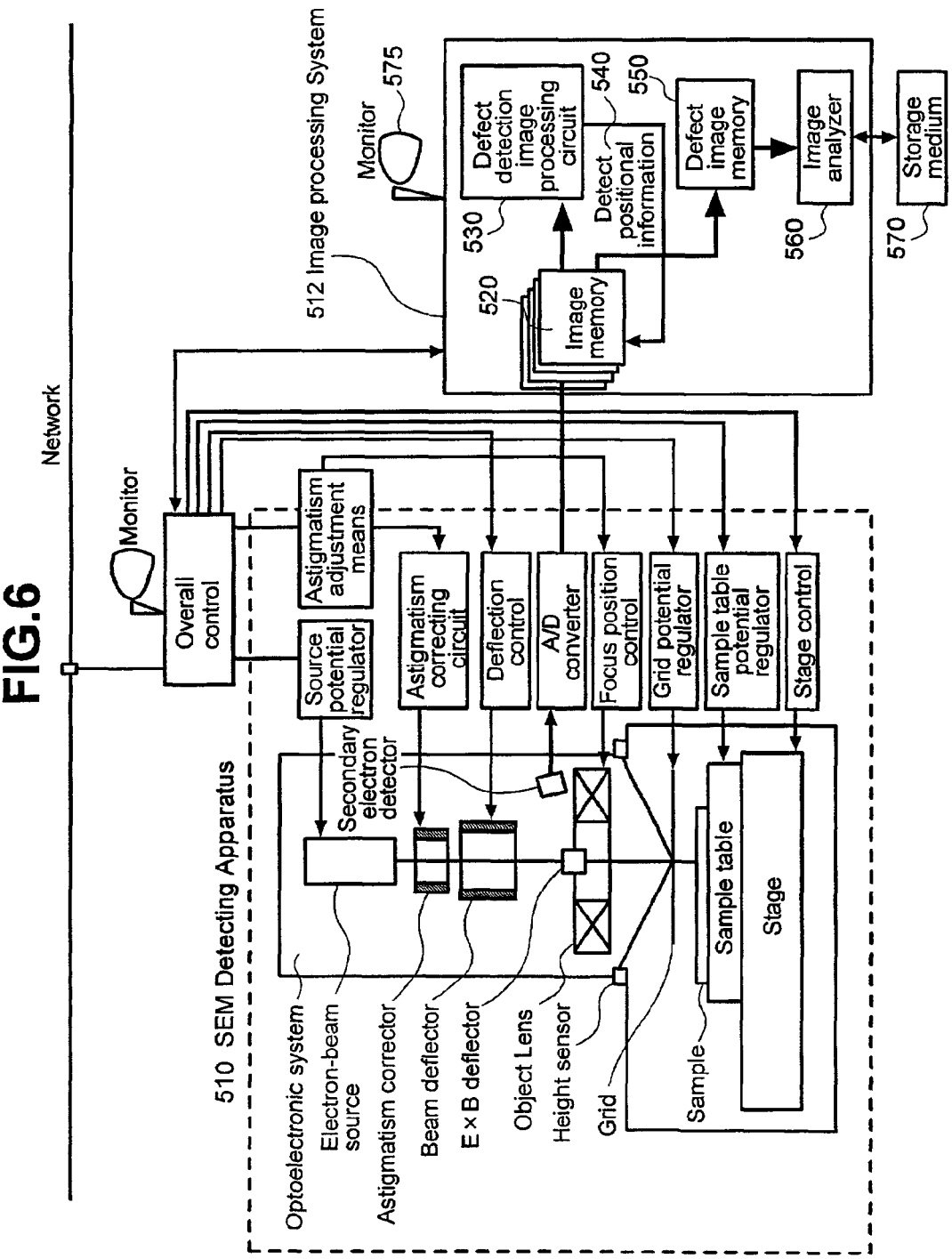
FIG. 6 shows an inspection system for another embodiment of the present invention.

FIG. 6 shows an inspection system for another embodiment of the present invention. The SEM Detecting Apparatus 510 has a Semiconductor Electron Microscope (SEM) and is coupled with an Image Processing System 512, which analyzes the images from the SEM. The Image Processing System 512 includes an Image memory 520, a Defect Detection Image Processing Circuit 530, a Defect Image Memory 550, and an Image Analyzer 560. The Image Processing System 512 is coupled with a Monitor 575 and a non-volatile Storage Medium 570. The Image Memory 520 and the Defect Detection Image Processing Circuit 530 perform functions the same as or similar to the Defect Detection Processing Unit 410 of FIG. 5. The Image Analyzer 560 has functions similar to the Multiple Processor Elements 434 and System Software 438 of FIG. 5.

The SEM Detecting Apparatus 510 scans a wafer and records the images in Image Memory 520. In order to maintain a reasonable memory size, Image Memory 520 may be a fixed size queue or buffer. A defect candidate is located as the result of a comparison check performed by a Defect Detection Image Processing Circuit 530 using a reference image and an inspection image stored in the Image Memory 520. In one embodiment the reference image is subtracted from the inspection image and thresholded using an initial threshold th0. If there exists a binary defect image then a defect candidate exists. The defect candidate positional information 540 is calculated by Defect Detection Image Processing Circuit 530, and the Image Processing System 512 clips an image of the defect candidate out of the inspection image and clips a corresponding image out of the reference image and stores the clipped images into a Defect Image Memory 550. An Image Analyzer 560 performs defect analysis on the clipped images stored in the Defect Image Memory 550. In one embodiment defect analysis includes determining a new threshold th1 based on a difference distribution. The Image Analyzer 560 includes a multiprocessor system, having a plurality of processors, where each processor may concurrently analyze a set of clipped images, for example, a clipped inspection image, and a clipped reference image (optionally, a clipped defect candidate image may also be included).

In one embodiment the Image Analyzer 560 calculates a defect detection margin, herein also called "margin," from the clipped inspection image and the corresponding clipped reference image stored in the Defect Image Memory 550. The defect detection margin is a threshold range from the initial threshold level (for example, th0) to the maximum up to which the defect can be detected. By calculating the defect detection margin per defect candidate, inspection results can be viewed as the threshold setting changes and inspection need not be conducted again. The clipped images, defect positional information, and defect detection margins are written onto the Storage Medium 570. Media such as DVD, CD, and HD may be used as the storage medium 570. The storage medium may be accessed via a communications network.

Figure 7:
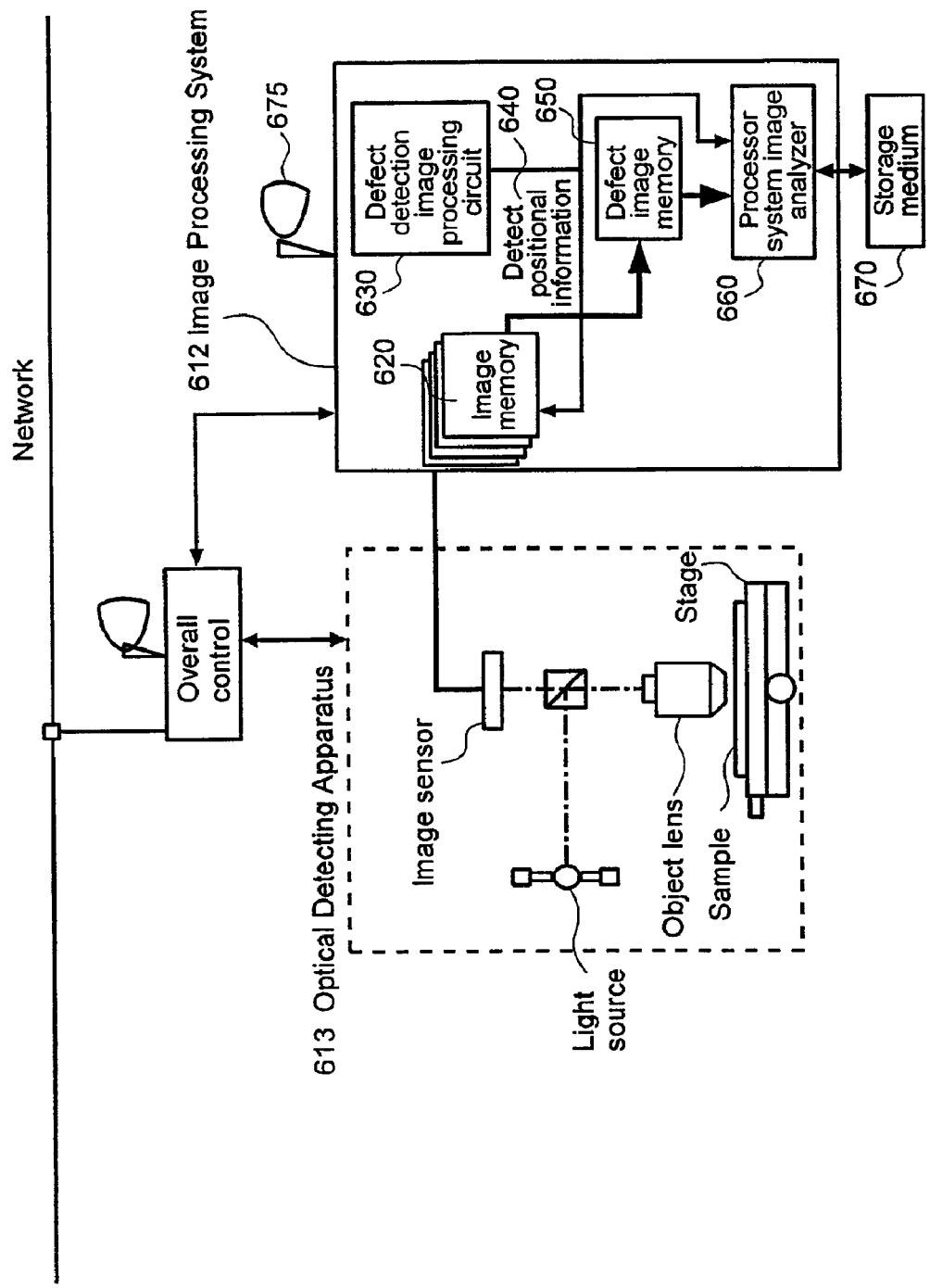
FIG. 7 shows an inspection system for yet another embodiment of the present invention.

FIG. 7 shows an inspection system for yet another embodiment of the present invention. The Optical Detecting Apparatus 610 has an optical device used to inspect semiconductors and is coupled with an Image Processing System 612, which analyzes the images from the an Optical Inspection Apparatus 610. The Image Processing System 612 includes an Image Memory 620, a Defect Detection Image Processing Circuit 630, a Defect Image Memory 650, and an Image Analysis System 660. The Image Processing System 612 is coupled with a Monitor 675 and a non-volatile Storage Medium 670. In effect the Image Processing System 612 is similar to the Image Processing System 512 for the SEM Detecting Apparatus 510. Thus embodiments of the Image Processing System of the present invention may be used with other detecting systems, for example, a Focus Ion Beam System, or a Transparent Electron Microscope (TEM) system, and are not limited to the embodiments for the SEM or Optical Detecting Systems described herein.

Figure 8:
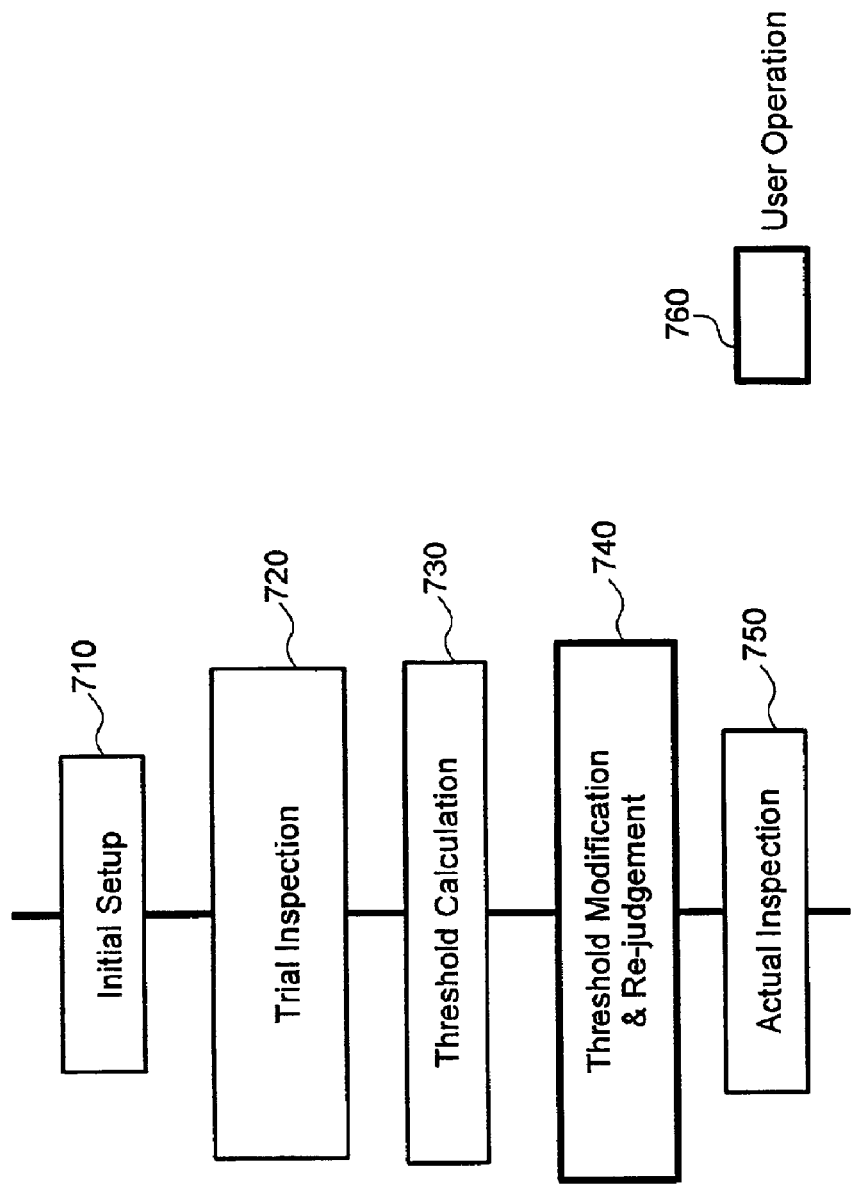
FIG. 8 shows a flowchart for a threshold set up method of an embodiment of the present invention.

FIG. 8 shows a flowchart for a threshold set up method of an embodiment of the present invention. At step 710, the initial threshold is set either manually by the user or automatically by the inspection system. The inspection system measures the electron beam 210 noise and uses the average electron beam noise as the initial threshold, th0. Next trial inspection (step 720) is performed by determining defect candidates, determining defect candidate information and images, and clipping the images. At step 730, another threshold (th1) is determined from defect analysis. The user views the results of the defect analysis, including a thresholded defect candidate distribution, on a GUI display on a monitor. Using this display the user verifies one or more of the defect candidates and may modify the threshold th1 (step 740) to, for example, a value th2. The Image Analyzer 560 calculates a new a thresholded defect candidate distribution for th2 and displays it on the monitor. As the Defect Image Memory 520 has the necessary defect candidate images and information, the user can reset thresholds, verify defects in images, and view the results without the need to rescan the wafer. Although optional re-scan of certain areas may be provided, it is not necessary. Thus as shown by the bolded User Operation box 760 in FIG. 8, the user is only needed at step 740. Once the threshold is determined, the actual inspection (step 750) is performed. At least one step, Threshold Modification and Re-judgement (step 740) may optionally be used in the actual inspection (step 750) to modify the threshold. In another embodiment step 740 is not used and th1 is used as the threshold for actual inspection.

In addition as the defect candidate images and information are stored on a non-volatile storage medium 570, this data may be used for after-inspection analysis. For example, the steps 710 to 740 can be repeated and analyzed to evaluate if a better threshold could have been determined. If so, then corrective measures on the process or on operator training may be instituted.

Figure 9:
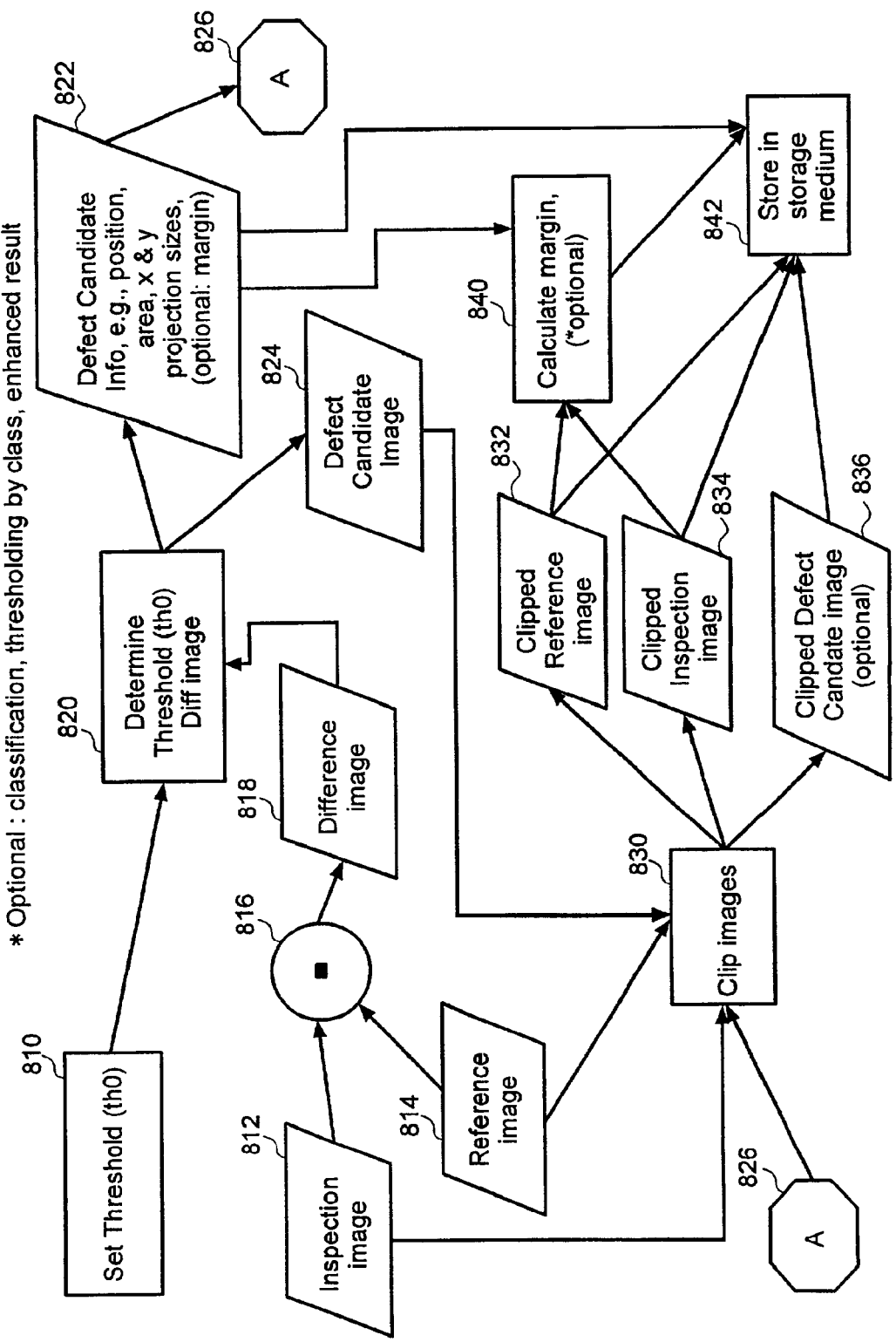
FIG. 9 show an expanded flowchart of the initial setup and trial inspection steps of FIG. 8 of an embodiment of the present invention.

FIG. 9 shows an expanded flowchart of the initial setup (step 710) and trial inspection (step 720) steps of FIG. 8. At process 810 the initial threshold (th0) is set either manually by the user or automatically using a standard metric for the system, for example, using electron beam noise. An inspection image 812, having a potential or candidate defect, and a reference image 814, corresponding to the inspection image 812, are subtracted 816 from each other to give a difference image 818. The initial threshold 810 is then used to threshold the difference image 818 (process 820) and to generate a binary defect candidate image 824 and defect candidate information 822, for example defect candidate position, defect candidate area, defect candidate x and y projection sizes, maximum difference between inspection and reference images, defect texture, reference texture, average difference inside a standard circle or average difference inside several selected standard circles in a pattern of repeated standard circles. In an alternative embodiment the margin may be calculated. The defect candidate information 822 is used at process 830 to clip the inspection image 812, the reference image 814, and the defect candidate image 824, resulting in a clipped reference image 832, a clipped inspection image 834, and a clipped defect candidate image 836. The clipped defect candidate image 836 is optional and is provided to assist the user in viewing the potential defect. Clipped reference image 832 and clipped inspection image 834 are used to calculate the margin in process 840. Note the margin could also have been calculated in an alternative embodiment at process 820. At process 840 optionally other calculations may be gone, for example, classification of the defect candidates, thresholding of the defect candidates by a type of defect, or an enhanced result. For an enhanced result a predetermined normal threshold thN is set. The normal threshold is greater than or equal to th0. The enhanced result for a defect candidate is the normal threshold thN subtracted from the defect candidate's maximum threshold (i.e., the largest threshold at which a defect candidate can be detected). The enhanced result is similar to a normalized value. The results of process 840, the defect information 822, the clipped reference image 832, the clipped inspection image 834, and the clipped defect candidate image 836, are stored in a non volatile storage media (process 842). In another embodiment only the margin is calculated in process 840 and stored in the storage medium (process 842). The other optional calculations, for example, classification of the defect candidates, thresholding of the defect candidates by a type of defect, or an enhanced result are done, using, for example, the stored data in storage medium 570, when the defect candidates are displayed, for example, in FIG. 18. In another embodiment, the only information calculated in process 840 is for example the first, second and third local maximums in the difference distribution graph. These are stored in the storage medium (process 842).

Figure 10:
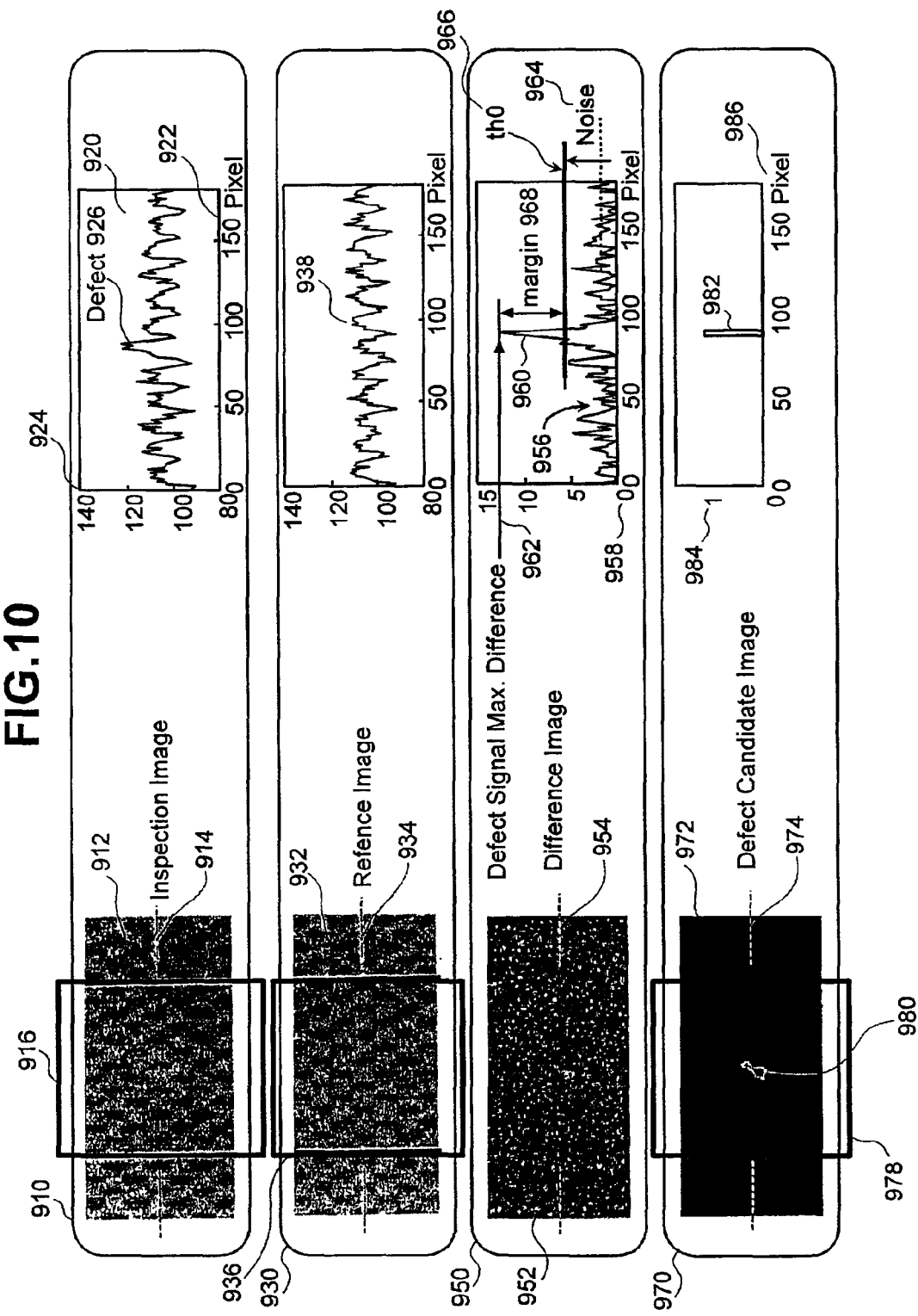
FIG. 10 gives an example of the initial setup and trial inspection.

FIG. 10 gives an example of the initial setup and trial inspection. In 910 an inspection image 912 having a cross-section 914 and clipped inspection image 916 are shown. The clipped inspection image 916 may have dimensions of 128×128 pixels. In 910 there is a graph 920 showing signal amplitude 924 versus pixel location 922 for cross-section 914. A defect candidate 926 is shown on graph 920. In 930, a reference image 932, a cross-section 934 of the reference image 932, and a clipped reference image 936 is shown. A graph 938 shows the background noise in reference image 932 along cross-section 934. In 950, a difference image 952 having a cross-section 954 is shown. The graph 956 has as its y-axis 958 the difference in signal amplitude from graphs 920 and 938. The defect candidate signal 960 associated with the defect candidate 926 has defect signal maximum difference 962. The noise 964 results from the difference in noise from inspection image 912 and reference image 932. The initial threshold th0 966 in one embodiment is manually or automatically set to the noise 964. The margin 968 is the difference between the defect signal maximum difference 962 and the threshold th0 966. In an 970 a defect candidate image 972, having cross-section 974, and a clipped defect candidate image 978 are shown. The defect candidate or potential defect 980 can be readily seen. In 970 a graph 982 with a binary amplitude 984 is shown for defect candidate image cross-section 974.

Figure 11:
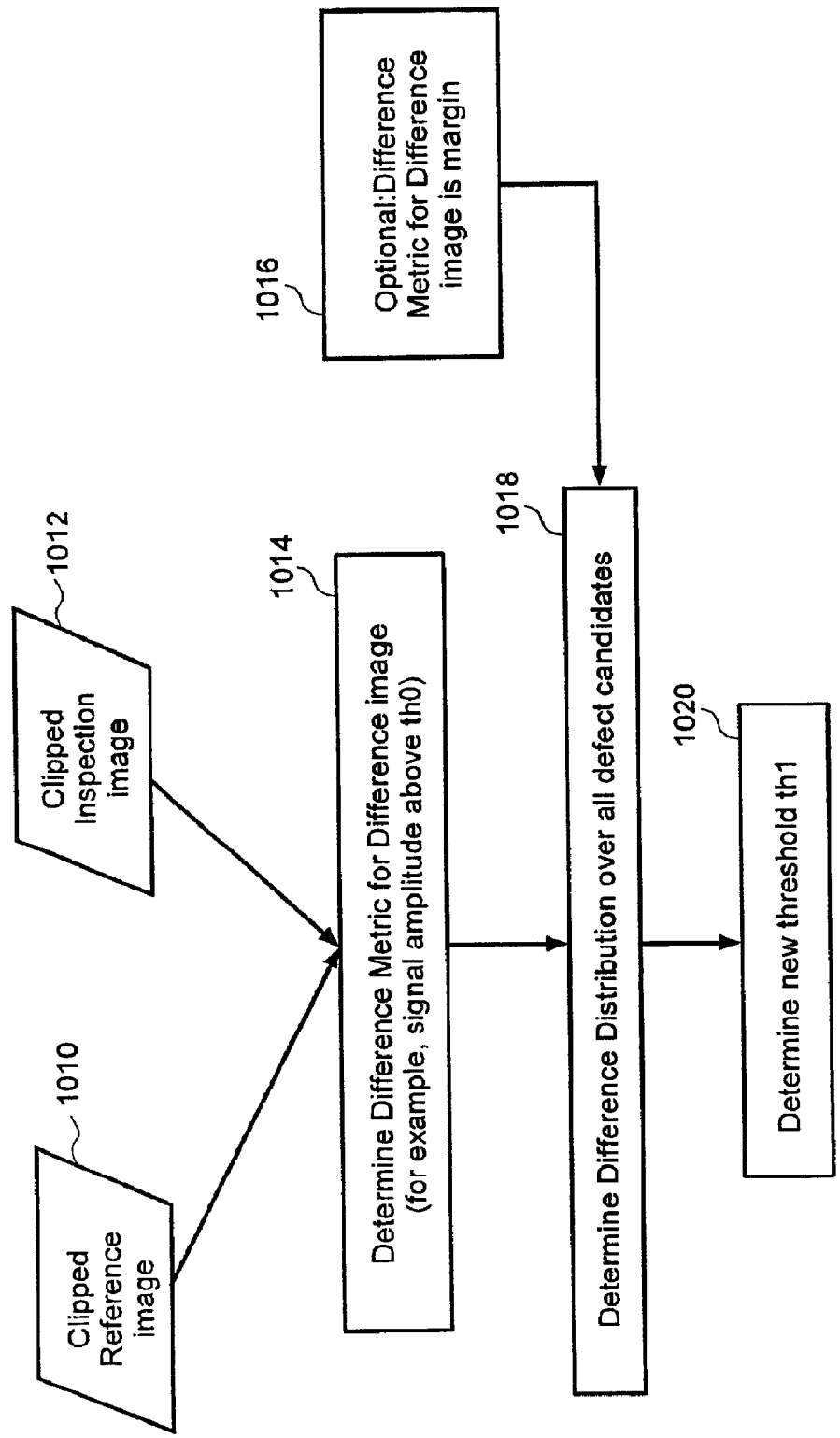
FIG. 11 shows an expanded view of the threshold calculation step of FIG. 8 of an embodiment of the present invention.

FIG. 11 shows an expanded view of the threshold calculation step 730 of FIG. 8. The clipped reference image 1010 and clipped inspection image 1012 are received at process 1014. These images are retrieved from the storage medium 570 or are used directly from FIG. 9 (images 832 and 834). At process 1014, first the clipped reference image 1010 is subtracted from the clipped inspection image 1012 to obtain a difference image. Next a difference metric is obtained from the difference image, for example, the signal amplitude above threshold th0 for a cross-section of the difference image is calculated. In an alternative embodiment the difference metric for the difference image is the margin (process 1016). The difference metric for each defect candidate is used to determine a difference distribution over all the defect candidates (process 1018). At process 1020 a new threshold th1 is determined, for example, using the first local minimum in the difference distribution. In another embodiment defect density, i.e., frequency per unit area, versus difference is first plotted. Next the area from a threshold thX to infinity is calculated for each difference, i.e., threshold, value. Where there is a plateau, i.e., the area does not substantially change, the defect density is determined to be stabilized and the threshold th1 is set at one of the plateau values. In another embodiment a fixed defect count or a fixed defect density may be set as th1. In yet another embodiment, a 3 DB point above the minimum at infinity may be set as threshold th1 in a defect density diagram such as 1452 in FIG. 15.

Figure 12:
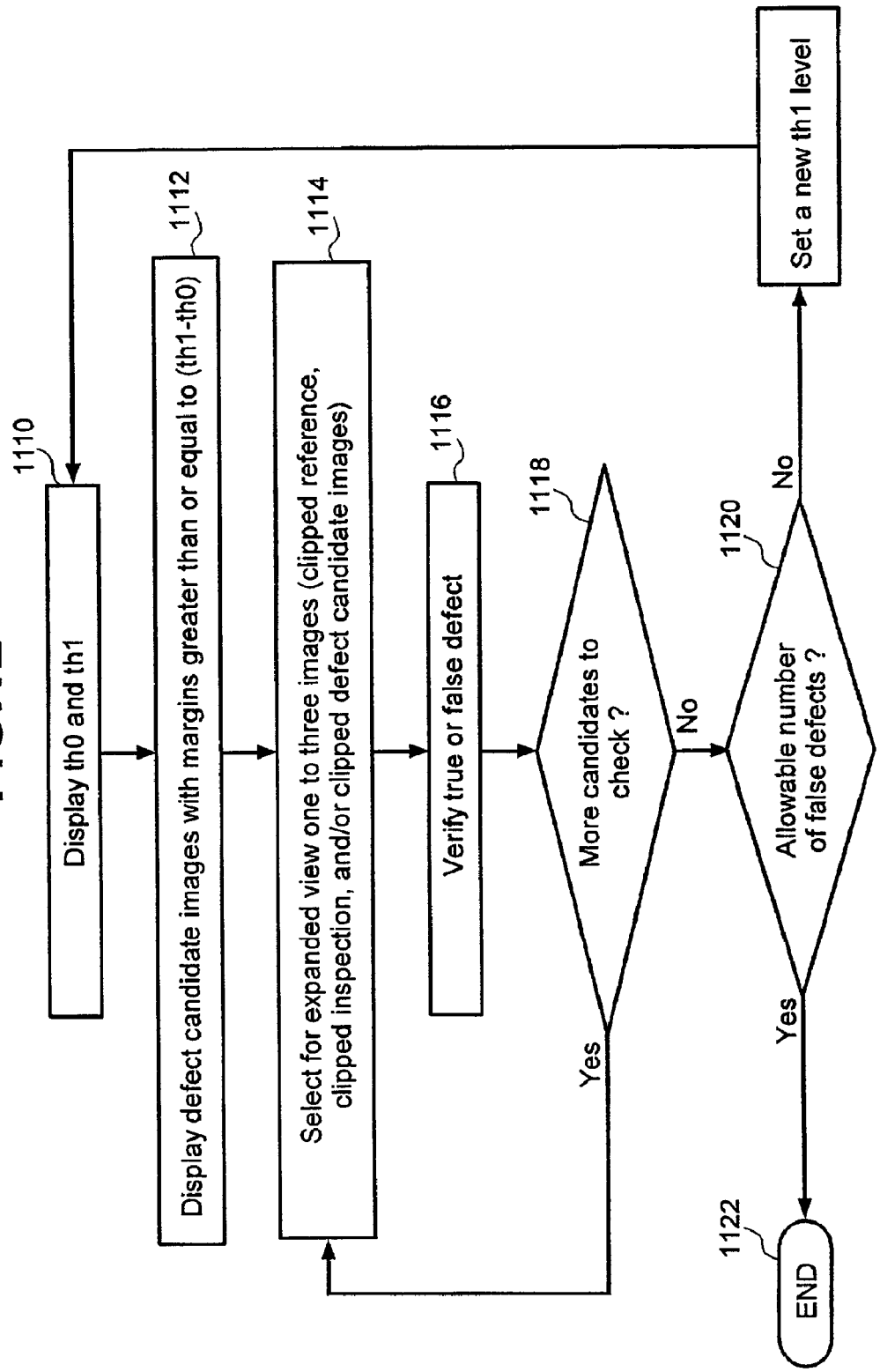
FIG. 12 show was an expanded view of the threshold modification and the judgment step of FIG. 8 of an embodiment of the present invention.

FIG. 12 shows an expanded view of the threshold modification and Re-judgment step 740 of FIG. 8. At process 1110 the initial threshold th0 and the threshold th1 calculated from step 730 are displayed. Next a two dimensional defect candidate difference distribution is displayed using symbols or indications representing defect candidate images with margins greater than or equal to (th1−th0). At process 1114 a symbol representing a defect candidate is selected for expanded view. One to three images, for example the clipped reference image, the clipped inspection image, and/or the clipped defect candidate image, may be displayed in another screen. Optionally the defect area may be SEM re-scanned and/or optical rescanned, and the corresponding image(s) displayed. The expanded image(s) of the defect candidate is verified by the user to be a true or false defect (process 1116). If there are more defect candidates to check (decision 1118) then process 1114 is returned to. If there are no more defect candidates to check then at decision 1120 it is determined if there are an allowable number of false defects. If there are allowable number of false defects, then the threshold setup process of FIG. 8 is complete (process 1122) and actual inspection is performed (step 750). If there are too many false defects, then at decision 1120 a new threshold level is set for th1 by the user and process 1110 is repeated.

Figure 13:
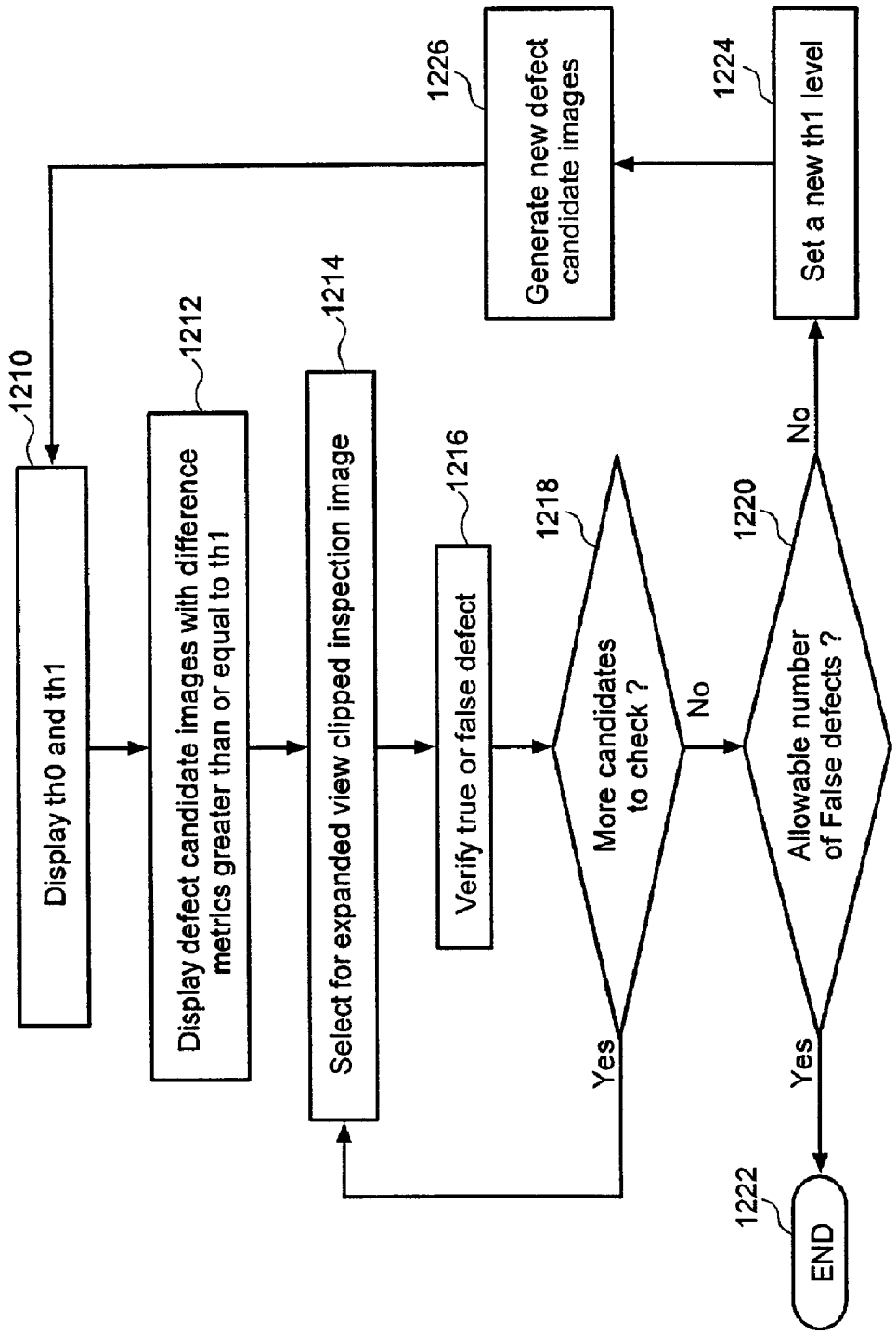
FIG. 13 shows an alternate embodiment of the threshold modification and judgment step of FIG. 8.

FIG. 13 shows an alternate embodiment of the Threshold Modification and Re-judgment step 740 of FIG. 8. At process 1210 thresholds th0 and th1 are displayed. At process 1212 defect candidate images with difference metric's greater than or equal to th1 are displayed. At process 1214 when an indication of a defect candidate image is selected for expanded view, the associated clipped inspection image is displayed. At process 1216 the user views the clipped inspection image and verifies if the defect candidate is a true or a false defect. At decision 1218 a test is made to see if there are more defect candidates to check. If yes then the process returns to process 1214. If no then the allowable number of false defects is checked (decision 1220). If there are an allowable number of false defects then the threshold setup process is finished (process 1222). If there are too many false defects, then the threshold level th1 is set to a new value at process 1224. At process 1226 new defect candidate images are generated and the process returns to process 1210.

Figure 14:
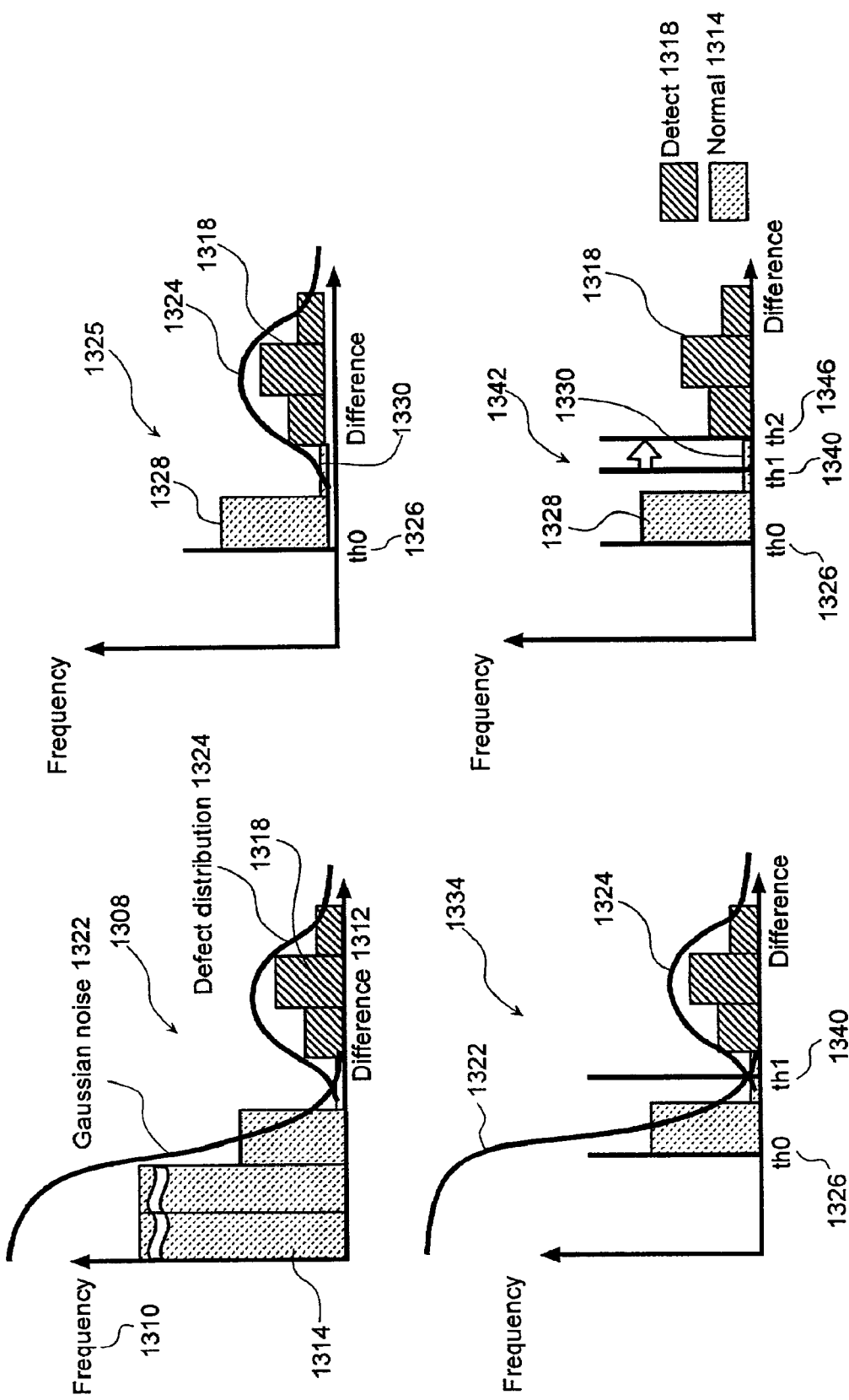
FIG. 14 gives an example of the threshold setup method of an embodiment of the present invention.

FIG. 14 gives an example of the threshold setup method of an embodiment of the present invention. The graph 1308 shows frequency 1310 versus the difference metric 1312. Graph 1308 includes a sub-graph 1322 showing a Gaussian noise distribution and sub-graph 1324 showing a defect distribution. The area 1314 under the Gaussian noise curve 1322 is a normal frequency distribution without any defects. The area 1318 under the defect distribution curve 1324 gives the frequency of defects at a specified threshold. Graph 1308 represents all the differences prior to any thresholding. Graph 1325 shows the results of the initial setup and trial inspection steps 710 and 720 of FIG. 8. The initial threshold th0 1326 is set. All differences below the threshold th0 had been removed. The normal noise above threshold 1326 includes areas 1328 and 1330. Graph 1334 shows the results of the threshold calculation step 730 of FIG. 8. The new threshold th1 1340 is set as the first minimum or valley between curve Gaussian noise curve 1322 and defect distribution curve 1324. Graph 1342 shows the result of the Threshold Modification and Re-judgment step 740 of FIG. 8. This step 740 may be optional, but, if it is included, it uses user selection from a GUI to modify the threshold from threshold th1 1340 to threshold th2 1346. For this example the optimal threshold, thresholds out areas 1328 and 1330 as they are noise and retains the defect area 1318. In this example the optimal threshold is th2.

Figure 15:
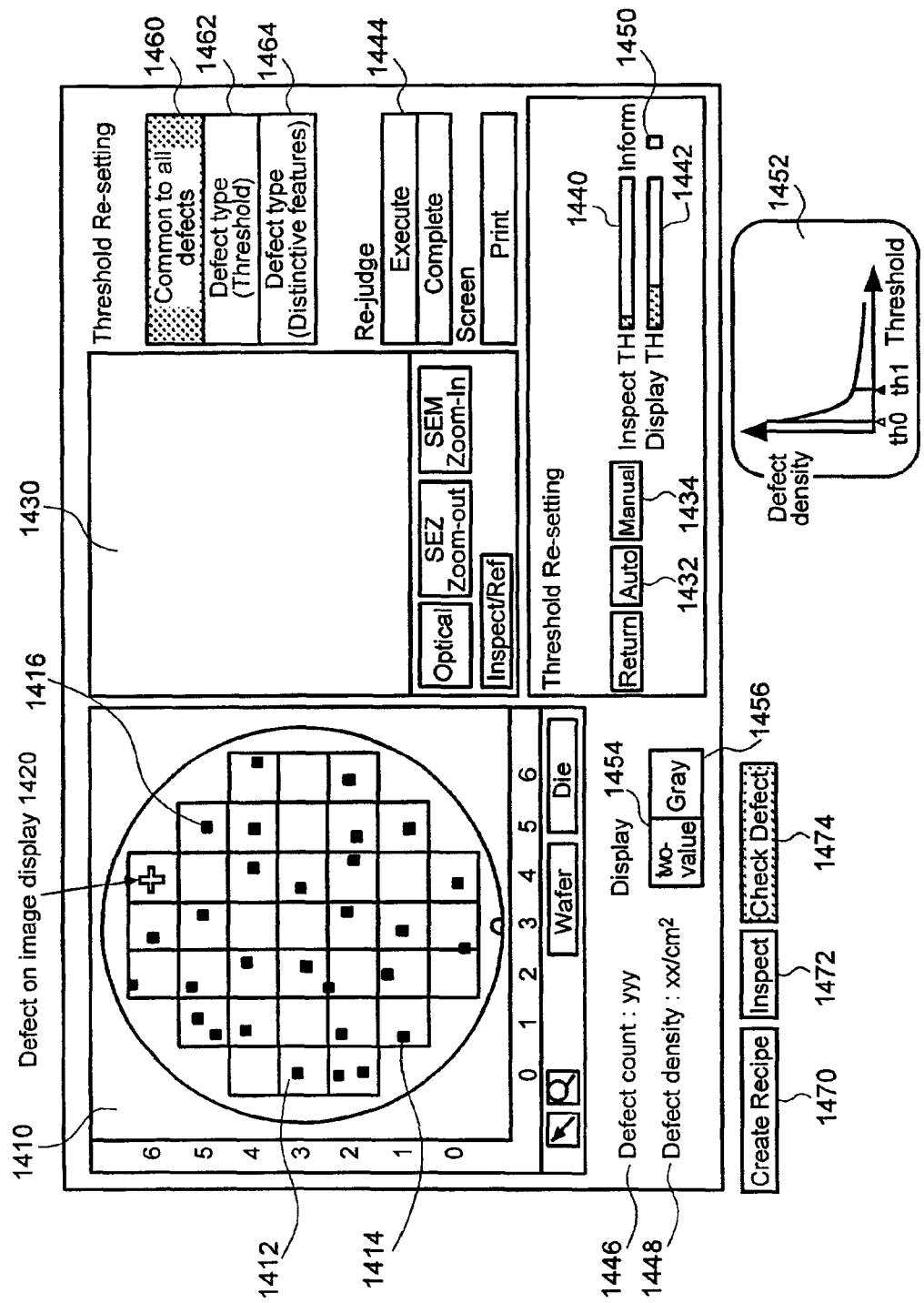
FIG. 15 is a schematic view of a GUI display used in the Threshold Modification and Re-judgement step of FIG. 8 of an embodiment of the present invention.

FIG. 15 is a schematic view of a GUI display used in the Threshold Modification and Re-judgement step 740 of FIG. 8 of an embodiment of the present invention. The GUI is used for checking inspection results after trial inspection and threshold calculation of th1. On a map display area 1410 on the display, the small solid square marks, for example, 1412, 1414, 1416, and 1420, indicate the locations of detected defect candidates. When one of these marks (i.e., symbols) is selected, for example, 1420, and dragged to the expanded image display area 1430, the clipped inspection image of the defect candidate stored in the defect image memory 550 is displayed in the expanded image display area 1430. A defect category input box, not shown on figure, is also displayed on the GUI. Defect category examples are hole missing, high impedance, foreign particle, and short circuit. In another embodiment, the clipped inspection image, the clipped reference image, the clipped defect candidate image or any combination thereof, may be shown in the expanded image display area 1430. In an alternate embodiment a re-scanned SEM and/or a re-scanned optical image(s) of the defect area may be displayed. In a further embodiment, if these images are in the Image Memory 520 a re-scan may be skipped and the images recalled from memory.

Buttons 1432 and 1434 allows a choice of automatic 1432 or manual 1434 threshold re-setting. In this example, it is assumed that the Auto button 1432 is chosen. On horizontal bar 1440 there is an initial threshold of th0 that has been preset before trial inspection and on horizontal bar 1442 there is a recommended threshold of th1 that has been automatically calculated, for example at step 730 of FIG. 8. When the Execute button 1444 is selected, the defect candidates which have defect detection margins greater than or equal to (th1–th0) are shown on map display area 1410. The values of defect count 1446 and defect density 1448 are also updated accordingly. In an alternative embodiment, the th1 threshold is applied to the difference of the clipped inspection and corresponding clipped reference images stored in defect image memory 550 for each defect candidate image. The plurality of processing elements in Image Analyzer 560 allow many of these calculations to occur in parallel. On the map display area 1410, the defect candidate marks relating to the th1 threshold are shown, and the values of defect count 1446 and defect density 1448 are also updated accordingly. In another embodiment, the defect distribution is shown for a range of margins; for example, thL<defect detection margin<thH, where thL, thH are low and high thresholds, respectively.

When the Inform button 1450 is chosen, a graph 1452 showing the relation between the threshold (e.g., th0 and th1) and the defect density is displayed and this graph 1452 provides information that can be used for judging whether the new threshold of th1 is proper.

If the Manual select button 1434 is chosen, the threshold th1 may be changed by sliding the Display TH bar 1442. When the Execute button 1444 is pressed after selecting another threshold, the defect candidate marks and the values displayed in the area 1410 and the values of defect count 1446 and defect density 1448 are updated to those in accordance with the result of inspection to which the threshold set by the slide position 1442 is applied. Buttons 1454 and 1456 allows the choice of two-value 1454 or multilevel (grayscale) 1456 for the defect candidate marks on the map display area 1410. If multilevel 1456, is chosen, a gray scale display in which the greater the defect detection margin the darker the defect candidate mark, is presented. The multilevel display is used for reference, when the th1 threshold is manually set and shows how dark defect candidates and light defect candidates are distributed on the wafer. In another embodiment a color code, mark size, mark shape code may be used instead of the grayscale. In yet another embodiment the greater the difference above the threshold th0 (i.e., the greater the defect detection margin) the lighter the defect candidate mark. For example, if the difference represented electrical resistance then the lighter the defect candidate mark, the lower the resistance. A very light mark may indicate a short circuit, while a very dark mark an open circuit.

Create Recipe button 1470 allows the use of a recipe or program script that sets the inspection mode in either die to die or array for various sections of the wafer 100. The Inspect button 1472 allows use of this GUI in actual inspection. And the button Check Defect allows use of this GUI in after inspection analysis.

According to this example, the user can easily view trial inspection results after threshold setting change without conducting the trial inspection again as in the conventional system, and therefore can greatly save time as compared with conducting the inspection again. In addition, this threshold setting process may be used during actual inspection to make adjustments. Thus this method is more flexible.

As the clipped images are stored in storage medium 570, it is also possible to do after inspection analysis of the defects. Thus the defect inspection process can be examined for improvements. Data is also available to assist in determining future initial threshold values. Thus efficiency may be improved.

Figure 16:
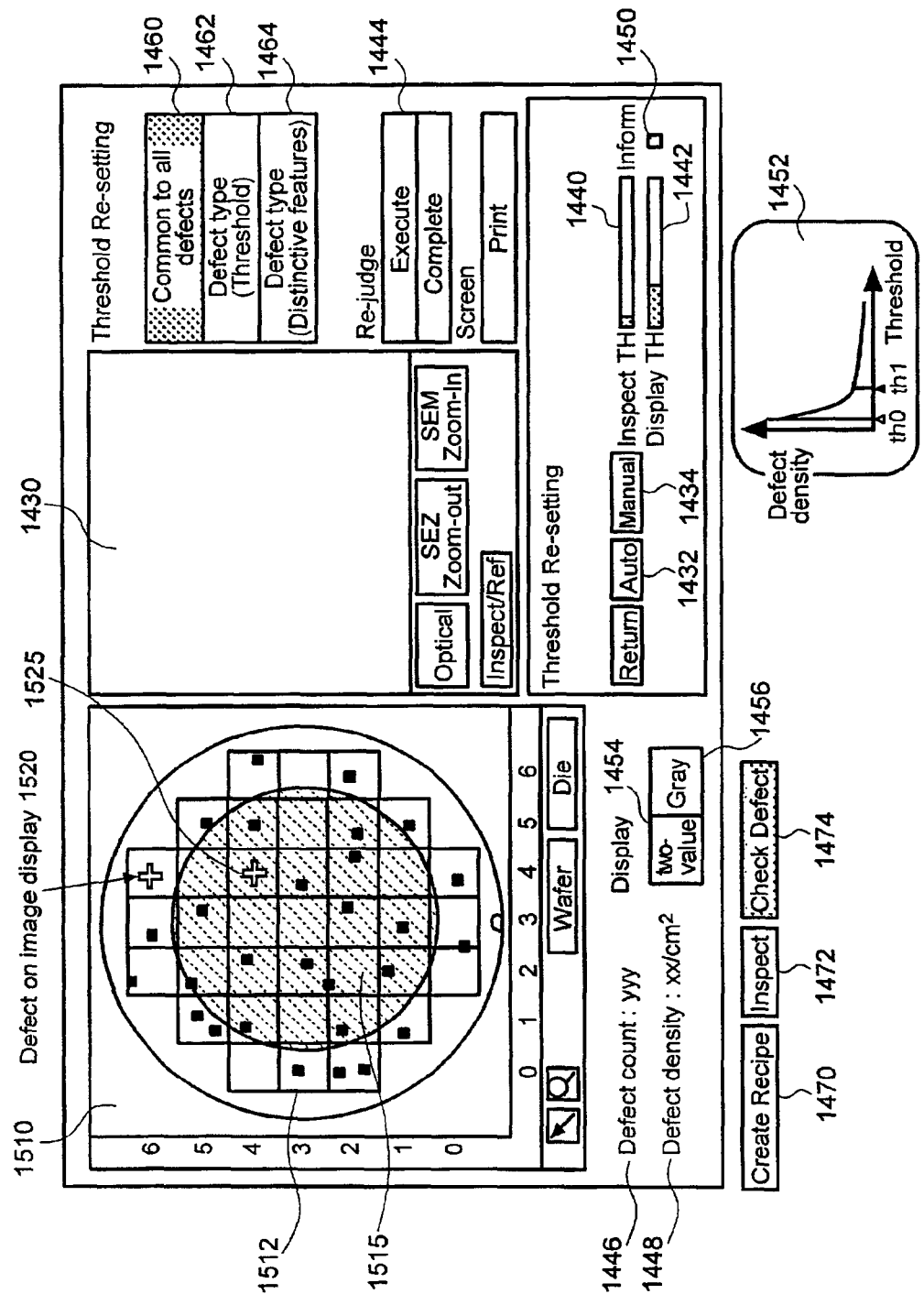
FIG. 16 shows a GUI of another embodiment of the present invention.

FIG. 16 shows a GUI of another embodiment of the present invention. In this embodiment the user can select which sections of the defect distribution screen 1510 uses what threshold. For example in screen 1510, there are two concentric circle areas shown, the outer circle 1512 and the inner circle 1515. A defect candidate 1520 in outer circle 1512 may be thresholded for display at a different threshold than defect candidate 1525 in the inner circle 1515. Threshold bars, for example, 1440 and 1442 could be assigned to the outer circle 1512 and inner circle 1515, accordingly.

Figure 17:
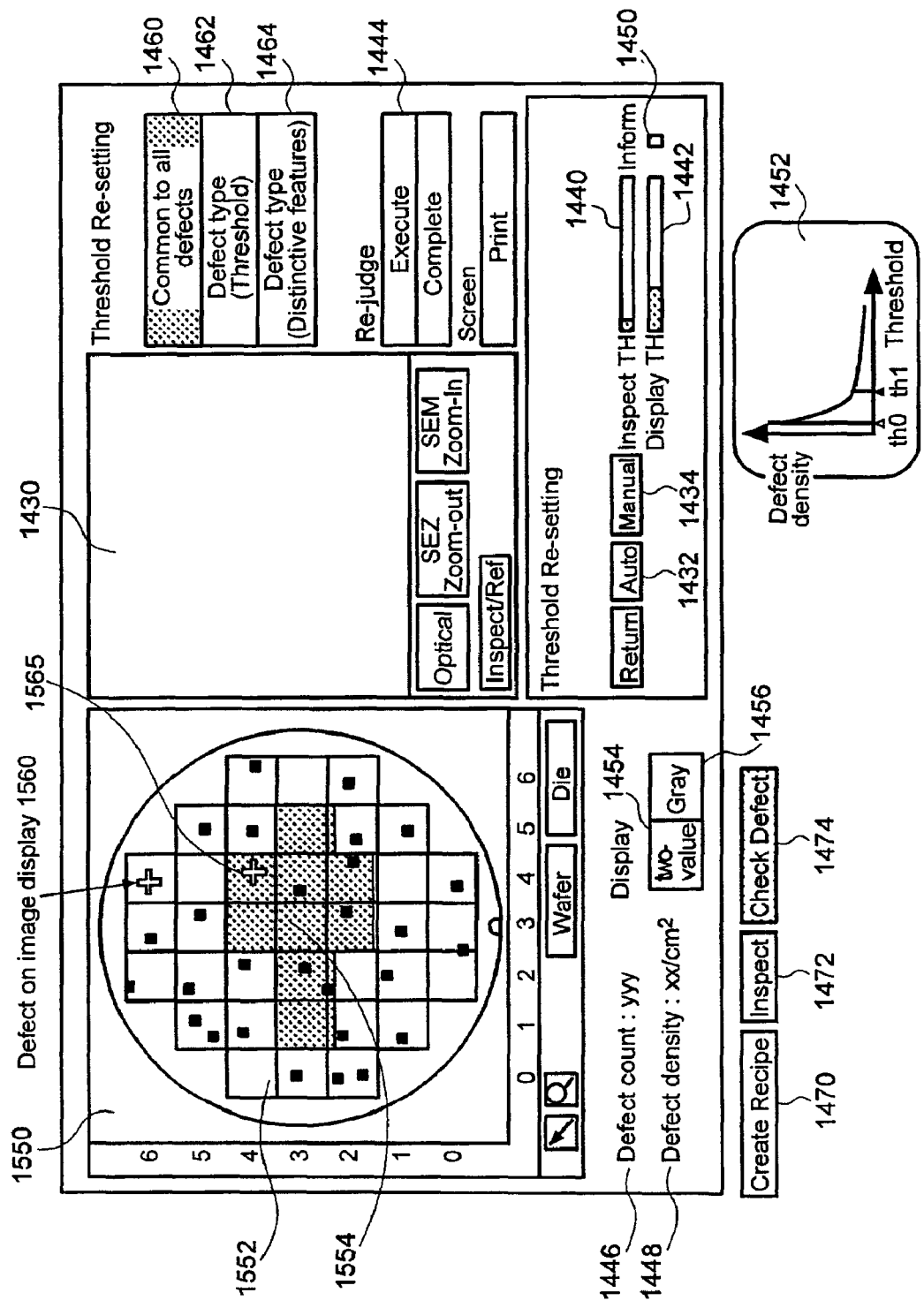
FIG. 17 shows a GUI of yet another embodiment of the present invention.

FIG. 17 shows a GUI of yet another embodiment of the present invention. In this embodiment the user can select an arbitrary section 1554 (dark dotted area) of the defect distribution screen 1550 for use with one threshold, while the remainder of the screen 1552 uses another threshold. The area may be selected by use of a mouse outlining the area to be selected. A defect candidate 1560 may be thresholded for display at a different threshold than defect candidate 1565 in selected area 1554. Threshold bars, for example, 1440 and 1442 could be assigned to the selected area 1554 and the remainder 1552 accordingly.

In another embodiment of the present invention, the image analyzer 560 determines distinctive features of a defect candidate, for example, its lightness, circumference, boundary unevenness, orientation, and position on the background pattern and then uses these features to classify the type, for example, open contact hole, short-circuit, foreign particle, or thin film residue, of the defect candidate image. The present embodiment is particularly intended to enable the user to view the results of inspection per defect type and to allow the user to set individual thresholds based on defect type.

An example of how to classify defects is described below. If, for example, holes of a memory device are assumed to be inspected, an open contact hole (open circuit) tends to look darker than a normal hole and a short-circuited hole tends to look lighter than a normal hole. The image analyzer 560 determines average lightness of a defect location as a distinctive feature of the defect by using the margin. Using this feature, the image analyzer 560 classifies the defect candidate as open contact hole or short-circuit. In an alternative embodiment the image analyzer 560 determines average lightness of a defect location as a distinctive feature of the defect by using the clipped inspection image and the corresponding clipped reference image stored in the defect image memory 550. In another embodiment, there are two defect distribution display formats and the GUI has a toggle button to switch between the two formats. One format is an automatically classified defect type and the other format is a manually classified defect type.

Figure 18:
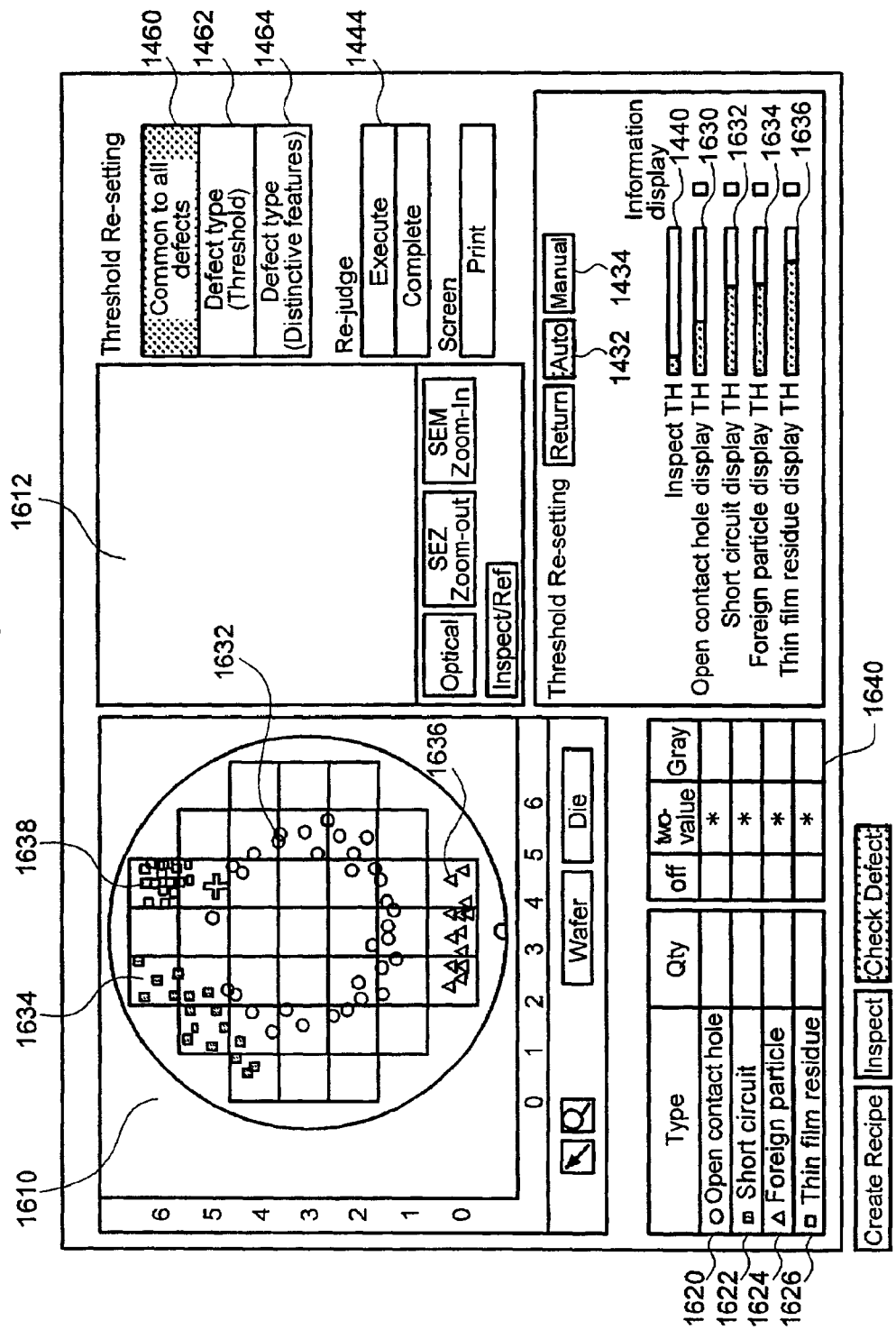
FIG. 18 shows a display of an embodiment of the present invention having defect candidate images classified according to type.

FIG. 18 shows a display of an embodiment of the present invention having defect candidate images classified according to type. On the map display area 1610, different marks or symbols for different defect types indicate the detected defects classified into four types: open contact hole 1620, short-circuit 1622, foreign particle 1624, and thin film residue 1626. In display area 1610 are shown examples of an open contact hole defect candidate 1632, a short-circuit defect candidate 1634, a foreign particle defect candidate 1636, and thin film residue defect candidate 1638.

The defect type (thresholded) button 1462 is assumed to be selected for this display. If the common to all defects button 1460 is selected then only a common defect is shown for all defect candidates and the display looks more like 1410 of FIG. 15 in format.

When the automatic threshold re-setting method is chosen by using the button 1432, new thresholds for all defect types are calculated and the results are shown on the horizontal bars 1630, 1632, 1634, and 1636 for the defect types 1620, 1622, 1624, and 1626 respectively. The automatic new threshold calculation method is the same as described for the previously embodiment for one type. On the other hand, if the Manual button 1434 is chosen, the desired thresholds for all defect types may be set by the user by sliding the horizontal bars 1630, 1632, 1634, and 1636 for the defect types.

A table 1640 allows the selection of a display view per defect type for displaying the defect candidate symbols on the map. That is for each defect type, a mutually exclusive choice of "off," two-value," or "gray" may be selected. If you choose "off" for a first defect type, defect locations classified into the first defect type are not displayed on the map. If you choose "two-value" for a second defect type, a two-value mark, for example, binary, is displayed for defect candidates of that type on the map. If you choose multilevel for a third type, the marks of the defect candidate for the third type, become darker or lighter, according to the defect detection margin specific to an individual defect candidate when being displayed. In another embodiment all defect types may be "off," "two-valued," or "gray" together. In another embodiment, a multi level display would include a circle, if th0<defect margin<th1, a triangular, if th1<defect margin<th2, or a rectangular, if th2<defect margin<th3.

The present embodiment enables the user to set inspection sensitivity, according to the defect type, so that inspection of all defect types with sensitivity suitable for each of the types can be conducted. This can solve the problem that inspecting defects of one type results in the detection of too many defects, because the sensitivity for detecting another defect type is too high.

Figure 19:
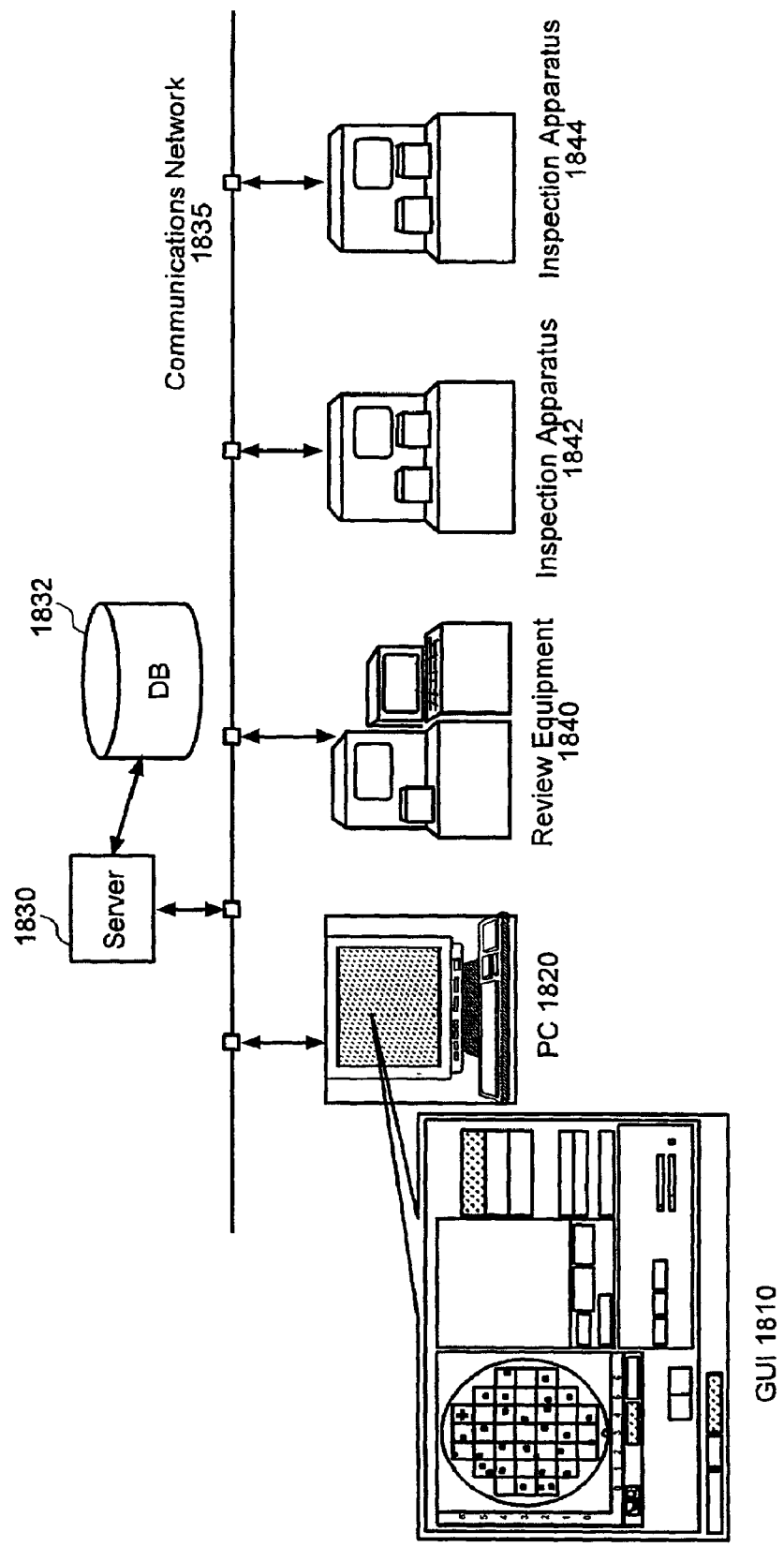
FIG. 19 shows a distributed system for an embodiment of the present invention.

FIG. 19 shows a distributed system for an embodiment of the present invention. The GUI display 1810 as shown, for example, in FIG. 15, may run on a Personal Computer (PC) 1820 as a client program. The PC 1820 is connected with a server 1830, having a DataBase (DB) 1832 via a Communications Network 1835. The Communications Network 1835 may be, for example, an intranet, Local Area Network (LAN), or the Internet. The Internet may be used if the analysis facility, having the PC 1820 and Server 1830, are located in one location, for example one country, and the manufacturing facility, having the Inspection Apparatuses 1842 and 1844, are in another location, for example another country. The DB 1832 includes the information stored in the storage medium by process 842 of FIG. 9, for example, the clipped images, margin, and the defect candidate information. The DB 1832 may serve as the storage medium 570 in FIG. 6. The Server 1830 then provides the images and data to the PC 1820, Review Apparatus 1840, Inspection Apparatus 1842, and Inspection Apparatus 1844 via Communications Network 1835. Thus defect images, information, and defect detection margins stored in a storage medium, i.e., DB 1832 can be referenced from anywhere via the Communications Network 1835.

The Image Processing System, such as 512 in FIG. 6, is in Inspection Apparatus 1842. Inspection Apparatus 1842 further includes a detecting apparatus, for example, a SEM Detecting Apparatus 510. Inspection Apparatus 1844 may have a SEM Detecting Apparatus 510 or an Optical Detecting Apparatus 610 or a combination as shown in U.S. Pat. No. 6,087,673, "Method for Inspecting Pattern and Apparatus Thereof," by Shishido, et. al., issued Jul. 11, 2000. Review Equipment 1840, which is optional, also has a detecting apparatus and in addition, a computer, to rescan a wafer off-line from the manufacturing process. Review Equipment 1840 is used to analyze previous defect candidate verification judgements and/or to classify the defects. In an alternative embodiment, the Server 1830, rather than Inspection Apparatus 1842, includes the Image Processing System, for example, 512 of FIG. 6 or Defect Image Processing Unit 430 of FIG. 5. The DB 1832 can store besides the storage medium 570 contents, also the Image Memory 520, and/or Defect Image Memory 550 data. The Server 1830 may also include Multiple Processor Elements 434.

Figure 20:
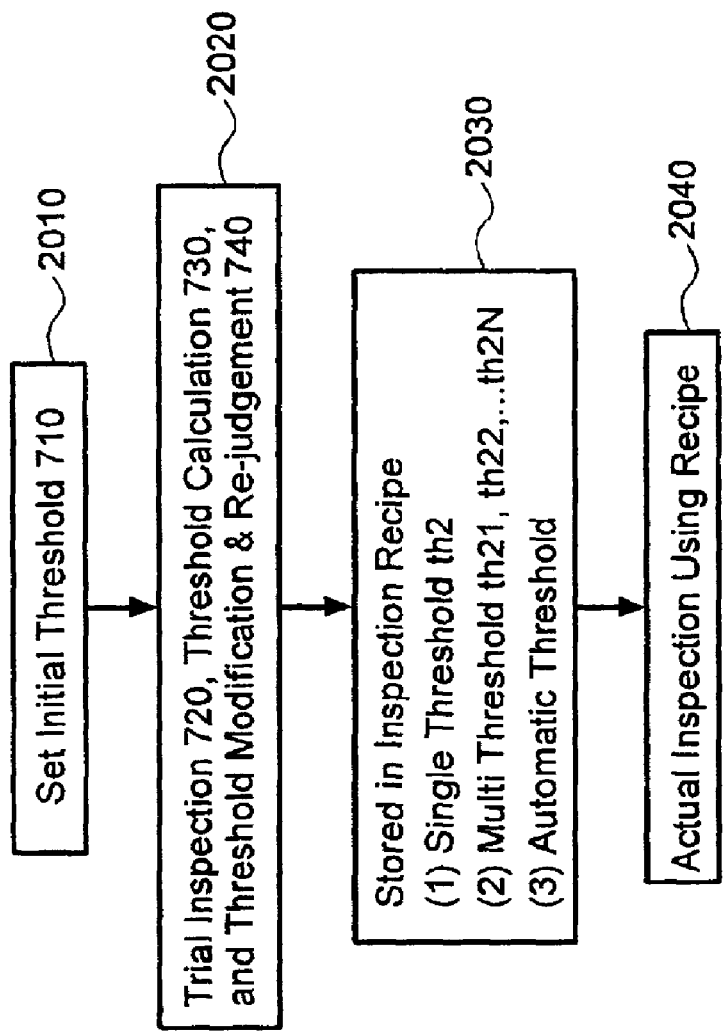
FIG. 20 shows a flowchart for using a stored recipe in actual inspection of an embodiment of the present invention.

FIG. 20 shows a flowchart for using a stored recipe in actual inspection of an embodiment of the present invention. Steps 2010 and 2020 include the steps 710 to 740 of FIG. 8. As illustrated by the example of FIG. 14, the result of threshold modification, and re-judgement (step 740), is threshold th2. By selecting Create Recipe 1470 in FIG. 15, this single threshold th2 can be stored in an inspection recipe (step 2030). Other examples of stored inspection recipes are Multi thresholds th21, th22, . . . th2N, and, automatic threshold (step 2030). Also a mixed mode of the above two or three recipe examples can be used. Using the stored recipe actual inspection is performed (step 2040) by selecting the Inspect 1472 button in FIG. 15.

FIG. 21 shows thresholds that may be used in actual inspection 2130 of an embodiment of the present invention. Referring to FIG. 21, Inspection Threshold 2110 corresponds to the bar in Inspect TH 1440 in FIG. 15 and Display Threshold 2112 corresponds to the bar in Display TH 1442 in FIG. 15. As indicated above, the results of threshold setup 2120 is an inspection threshold 2110 of th0 2122 and a display threshold 2112 of th2 2124.

In one embodiment of using the single threshold, th2, recipe, in actual inspection the threshold of the defect detection image processing circuit 530 is fixed at th2 and no image analyzer unit 560 is used. Thus the display threshold 2112 is essentially fixed and not user modifiable. In another embodiment the threshold of the defect detection image processing circuit 530, i.e., inspection threshold 2110, is set at (th2-α) 2132, where α is an instrument constant, for example, about 3 to 6 times the standard deviation of the electron beam noise. The display threshold is then th2 2134 and is user modifiable during actual inspection 2130.

Using the multi threshold recipe, the threshold of defect detection processing unit is ((minimum th1, th2, . . . , thN)-α) 2136 and the display threshold 2112 shown on the GUI as buttons th21 2138, th22 2140, or thN 2142. In this case on actual inspection 2130, the operator can either select one of the buttons th21, th22, . . . , th2N or modify the threshold using the Display TH bar 1442 of FIG. 15, which is initially set to the selected button. Outputs of multi threshold means plural inspection results can be obtained at the same time.

FIG. 22 shows an example of defect difference distributions of an embodiment of the present invention. The axes are difference 2212, for example signal amplitude difference between the inspection and reference images, and frequency 2214. The distribution 2220 represents differences for normal background noise. The distribution curve 2222 illustrates slight defect differences, and the distribution curve 2224 illustrates large defect differences. In this embodiment the result of step 1020 of FIG. 11 is not one threshold but many, th11, th12, or th1N. These thresholds are automatically calculated by step 730 of FIG. 8 and represent the local minimums of the difference distribution. During Threshold Modification and Re-judgement (step 740), these may be directly used as th21, th22, or th2N, respectively or user modified similar to the example shown in FIG. 14 to give th21, th22, or th2N. From FIG. 22 if the operator selects threshold th21 2230, then slight defect differences 2222 can be detected along with many false defects (high sensitivity). If threshold th22 2232 is chosen, then only defects with large differences 2224 are detected (low sensitivity). During the setup phase, slight difference detection, for example threshold th21, is used.

Using automatic thresholding 2146, (th2-α) 2144 is used as the inspection threshold 2110 (i.e., initial setup threshold in step 710), and the same threshold calculation given in Threshold Calculation step 730 is applied to determine the threshold 2146 for actual inspection 2130.

Another embodiment of the present invention provides for a computer program product stored on a computer readable medium for inspecting a specimen. The program includes: code for setting a threshold value; code for detecting a detected image of a specimen; code for comparing the detected image to a reference image; code for extracting from the comparing, a defect candidate using the threshold value; code for storing an information of the defect candidate to a memory; code for setting a new threshold value; and code for extracting a defect from the defect candidate using the stored information and the new threshold value.

In yet another embodiment a computer program product stored on a computer readable medium for inspecting a circuit pattern on a semiconductor material is provided. The program includes: code for setting an initial threshold; code for detecting an inspection image; code for determining defect candidate information by thresholding a comparison between said inspection image and a reference image, wherein said thresholding uses said initial threshold; code for determining a new threshold using said defect candidate information; and code for evaluating a defect in said inspection image using said new threshold.

Although the above functionality has generally been described in terms of specific hardware and software, it would be recognized that the invention has a much broader range of applicability. For example, the software functionality can be further combined or even separated. Similarly, the hardware functionality can be further combined, or even separated. The software functionality can be implemented in terms of hardware or a combination of hardware and software. Similarly, the hardware functionality can be implemented in software or a combination of hardware and software. Any number of different combinations can occur depending upon the application.

Many modifications and variations of the present invention are possible in light of the above teachings. Therefore, it is to be understood that within the scope of the appended claims, the invention may be practiced otherwise than as specifically described.

What is claimed is:

1. A method for inspecting a specimen, comprising:
   setting a first threshold value;
   detecting an image of a specimen;
   comparing the image detected by said detecting to a reference image;
   extracting from the comparing, a defect candidate using the first threshold value;
   storing an information of the defect candidate to a memory;
   setting a second threshold value; and
   extracting a defect from the defect candidate using the stored information and the second threshold value,
   wherein said second threshold value is determined by using information of distribution of defect candidates extracted from the comparing by using the first threshold value.

2. A method of inspecting a specimen according to claim 1, wherein the information of the defect candidate stored in the memory includes at least one of the following: a defect candidate position, a defect candidate area, a defect candidate x and y projection size, a maximum difference between the detected image and the reference image, a defect texture, or a reference texture.

3. A method of inspecting a specimen according to claim 1, wherein the information of the defect candidate stored in the memory includes an image of the defect candidate.

4. The method of claim 1 wherein the specimen includes a circuit pattern on a semiconductor wafer.

5. A method for inspecting a circuit pattern on a semiconductor material comprising:
   setting an initial threshold value;
   detecting an image of a specimen;
   generating a difference image by comparing said image of a specimen detected by said detecting and a reference image;
   extracting defect candidate by thresholding said difference image, wherein said thresholding uses said initial threshold value;
   storing said image of a specimen in which said defect candidate is extracted by using said initial threshold value and a reference image in a memory;
   modifying said initial threshold value to a modified threshold value by using information on distribution of defect candidates extracted from the comparing by using the initial threshold value; and
   detecting a defect in said image stored in said memory using said modified threshold value.

6. A method according to the claim 5, further comprising displaying information on distribution of defect candidates extracted from the comparing by using the initial threshold value.

7. A method according to the claim 5, further comprising displaying in a map form a distribution of defect detected in said detecting by using the modified threshold value.

8. A method according to the claim 7, further comprising displaying an image of a defect candidate stored in the memory by designating a location on the map.

9. A method according to the claim 5, wherein in modifying said initial threshold value, said information includes a distribution of difference value between said image of a specimen and said reference image stored in said memory.

10. A method for inspecting a circuit pattern on a semiconductor material comprising:
    setting an initial threshold value;
    detecting an image of a specimen;
    comparing said image of a specimen detected by said detecting and a reference image and detecting a difference value between said image of a specimen and the reference image;
    extracting defect candidates from said detected difference value by using said initial threshold value;
    storing an image of a defect candidate extracted in said extracting and a reference image thereof in a memory;
    displaying on a screen a distribution of defect candidates extracted in said extracting; and
    modifying said initial threshold value by using information displayed on said screen and the images stored in the memory.

11. A method according to the claim 10, wherein in said displaying, a map of the distribution of defect candidates extracted in said extracting is displayed on the screen.

12. A method according to the claim 11, further comprising displaying an image of a defect candidate stored in the memory by designating a location on the map.

13. A method according to the claim 10, wherein in modifying said initial threshold value, said information includes a distribution of said detected difference value between said image of a defect candidate and said reference image stored in said memory.

14. A method for inspecting a circuit pattern on a semiconductor material comprising:
    setting a threshold value for inspecting a circuit pattern on a semiconductor material with an inspecting apparatus; and
    inspecting a circuit pattern on a semiconductor material with said inspecting apparatus,
    wherein setting the threshold value comprises:
      setting an initial threshold value for inspecting a circuit pattern on a semiconductor material with said inspecting apparatus;
      detecting an image of the circuit pattern with a detecting unit of said inspecting apparatus;
      generating a difference image by comparing an image of the circuit pattern detected by the detecting and a reference image;
      extracting defect candidate by comparing said difference image with said initial threshold value;
      storing said image of a specimen in which said defect candidate is extracted by using said initial threshold value and a reference image in a memory;
      modifying said initial threshold value by using information of distribution of defect candidates extracted from the comparing by using the initial threshold value; and
      setting a modified initial threshold modified by said modifying for inspecting a circuit pattern.

15. An apparatus for inspecting a specimen comprising:
    a first memory to store a first threshold value;
    a detecting unit to detect an image of a specimen;
    a comparator to compare the image detected by said detecting unit to a reference image;
    a first processor to extract a defect candidate from an output of said comparator by using the first threshold value;

a second memory to store information of the defect candidate extracted by said extractor;

a display to display said information of the defect candidate;

a third memory to store a second threshold value; and a second processor to extract a defect from the defect candidate by using the information stored in said second memory and the second threshold value stored in said third memory, wherein said second threshold value is determined by using information of distribution of defect candidates extracted from comparing said image detected to said reference image using the first threshold value.

16. An apparatus according to the claim 15, wherein said detecting unit detects a SEM image of a specimen.

17. An apparatus according to the claim 15, wherein said detecting unit detects an optical image of a specimen.

18. An apparatus according to the claim 15, wherein said detecting memory stores an image detected by said detecting unit in which said defect candidate is extracted by using said first threshold value and a reference image.

19. An apparatus according to the claim 15, wherein said display further displays information of the defect extracted by said second processor.

20. An apparatus for inspecting a specimen comprising:

a first memory to store an initial threshold value;

a detecting unit to detect an image of a specimen;

an image processor to generate a difference image by comparing said image of the specimen detected by said detecting unit and a reference image;

a defect image processor to extract defect candidate by thresholding said difference image generated by said image processor using said initial threshold value stored in said first memory;

a display to display said information of the defect candidate extracted by said defect image processor;

a second memory to store said image of a specimen in which said defect candidate is extracted by using said initial threshold value and the reference image;

a third memory to store a modified threshold value which is modified from said initial threshold value by using information of distribution of defect candidates extracted by said defect image processor using the first threshold value stored in said first memory; and a processor to detect a defect in said image stored in said second memory by using said modified threshold stored in said third memory.

21. An apparatus according to the claim 20, wherein said detecting unit detects a SEM image of a specimen.

22. An apparatus according to the claim 20, wherein said detecting unit detects an optical image of a specimen.

23. An apparatus according to the claim 20, wherein said second memory stores an image detected by said detecting unit in which said defect candidate is extracted by using said first threshold value and a reference image.

24. An apparatus according to the claim 20, wherein said display further displays information of the defect extracted by said second processor.

* * * * *